US010317403B2

(12) United States Patent
Ohshiro

(10) Patent No.: US 10,317,403 B2
(45) Date of Patent: *Jun. 11, 2019

(54) IMMUNOASSAY ANALYZER AND IMMUNOASSAY METHOD

(71) Applicant: ARKRAY, Inc., Kyoto (JP)

(72) Inventor: Kyouichi Ohshiro, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1376 days.

This patent is subject to a terminal disclaimer.

(21) Appl. No.: 13/756,882

(22) Filed: Feb. 1, 2013

(65) Prior Publication Data

US 2013/0143311 A1 Jun. 6, 2013

Related U.S. Application Data

(62) Division of application No. 12/995,075, filed as application No. PCT/JP2009/059757 on May 28, 2009, now Pat. No. 8,389,230.

(30) Foreign Application Priority Data

May 29, 2008 (JP) .................................. 2008-141759

(51) Int. Cl.
G01N 21/77 (2006.01)
G01N 21/78 (2006.01)
(Continued)

(52) U.S. Cl.
CPC ....... G01N 33/56983 (2013.01); G01N 21/78 (2013.01); G01N 21/8483 (2013.01);
(Continued)

(58) Field of Classification Search
None
See application file for complete search history.

(56) References Cited

U.S. PATENT DOCUMENTS 7,887,750 B2 2/2011 Blatt et al.
8,389,230 B2* 3/2013 Ohshiro ................ G01N 21/78
435/7.9
(Continued)

FOREIGN PATENT DOCUMENTS

CN 1964789 A 5/2007
JP 2000-0258418 A 9/2000
(Continued)

OTHER PUBLICATIONS

Stockton et al., "Multiplex PCR for Typing and Subtyping Influenza and Respiratory Syncytial Viruses," Journal of Clinical Microbiology, 36: 2990-2995 (1998).
(Continued)

Primary Examiner — Melanie Brown
Assistant Examiner — Richard Moerschell
(74) Attorney, Agent, or Firm — Morgan, Lewis & Bockius LLP

(57) ABSTRACT

The present invention provides an immunoassay analyzer capable of discriminating between normal coloring due to a specific immunoreaction and abnormal coloring due to a cause other than the specific immunoreaction in a measurement region of a sample analysis tool. An immunoassay analyzer 1 of the present invention includes an optical detection unit 4 and a determination unit 5. The optical detection unit 4 includes an optical signal measurement unit for measuring an optical signal at each of two or more different wavelengths including a main wavelength for detecting color change due to the specific immunoreaction and a sub-wavelength(s) other than the main wavelength. The determination unit 5 includes a discrimination unit for comparing the respective optical signals at the two or more different wavelengths and discriminating between the color change due to the specific immunoreaction and color change
(Continued)

due to a cause other than the specific immunoreaction based on a comparison criterion determined previously.

16 Claims, 6 Drawing Sheets

(51) Int. Cl.
 $G01N\ 21/84$ (2006.01)
 $G01N\ 33/543$ (2006.01)
 $G01N\ 33/569$ (2006.01)

(52) U.S. Cl.
 CPC . *G01N 33/54373* (2013.01); *G01N 33/56944* (2013.01); *G01N 2021/7773* (2013.01)

(56) References Cited

U.S. PATENT DOCUMENTS

| | | |
|---|---|---|
| 2004/0265800 A1 | 12/2004 | Imoarai et al. |
| 2005/0130236 A1 | 6/2005 | Goldman |
| 2005/0249633 A1* | 11/2005 | Blatt ............... B01L 3/5027 422/400 |
| 2006/0014302 A1* | 1/2006 | Martinez ............ G01N 21/474 436/518 |
| 2006/0154239 A1* | 7/2006 | Gassner ............ G01N 33/6896 435/5 |
| 2007/0004006 A1* | 1/2007 | Jung ..................... C12Q 1/701 435/69.1 |
| 2009/0269735 A1 | 10/2009 | Imoarai et al. |
| 2011/0091357 A1 | 4/2011 | Blatt et al. |

FOREIGN PATENT DOCUMENTS

| | | |
|---|---|---|
| JP | 2005-024323 A | 1/2005 |
| JP | 2007-333426 A | 12/2007 |
| JP | 2008-014751 A | 1/2008 |
| WO | 2005/116632 A2 | 12/2005 |

OTHER PUBLICATIONS

Zhang, "Detection and identification of human influenza viruses by the polymerase chain reaction," Journal of Virological Methods, 33: 165-189 (1991). (abstract).

Manesis et al., "Significance of Hepatitis B Viremia Levels Determined by a Quantitative Polymerase Chain Reaction Assay in Patients With Hepatitis B e Antigen-Negative Chronic Hepatitis B Virus Infection," American Journal of Gastroenterology, 98: 2261-2267 (2003).

Thanh et al., "Laser-based double beam absorption detection for aggregation immunoassays using gold nanoparticles," Anal Bioanal Chem, 374: 1174-1178 (2002).

Zhang Lixia, "ELISA detection technology," (2005).

Extended European Search Report issued in corresponding European Patent Application No. 09754758.2 dated Jun. 27, 2014.

Office Action issued in corresponding Japanese Patent Application No. 2009-541667 dated May 31, 2013.

Office Action issued in corresponding European Patent Application No. 09754758.2 dated Apr. 13, 2016.

\* cited by examiner

IMMUNOASSAY ANALYZER AND IMMUNOASSAY METHOD

TECHNICAL FIELD

The present invention relates to an immunoassay analyzer and an immunoassay method.

BACKGROUND ART

In recent years, in the diagnosis of infectious diseases, diagnostic kits for detecting pathogens such as bacteria and viruses are in widespread use. Among these diagnostic kits, a diagnostic kit utilizing an immunochromatography method is used widely because it can achieve measurement conveniently and rapidly. The principle of the measurement according to the immunochromatography method carried out using the diagnostic kit is as follows. First, a sample analysis tool (test piece) formed of a porous membrane and in which antibodies are immobilized on a measurement region of the porous membrane is provided. A sample (specimen) and labeled antibodies labeled with colored particles are added thereto. When antigens as a substance to be detected are present in the sample, the labeled antibodies and the immobilized antibodies form complexes via the antigens, whereby the measurement region on the porous membrane is colored by the colored particles, for example. The label may be, in addition to the colored particles, an enzyme, which is used in combination with a substrate that is colored through an enzyme reaction. The measurement region generally is in a line form. When coloring is observed, it is regarded that the substance to be detected is presence in the sample so that it is determined that the sample is positive. On the other hand, when no coloring is observed, it is regarded that the substance to be detected is not presence in the sample so that it is determined that the sample is negative. Such determination can be made through visual observation. However, in terms of objectivity and higher efficiency in determination, etc., an immunoassay analyzer that carries out determination by optically detecting the coloring of a measurement region of a sample analysis tool has been put to practical use (e.g., Patent Document 1 and the like). However, in the diagnostic kit utilizing the immunochromatography method, abnormal coloring, e.g., coloring due to a cause other than immunoreactions, such as coloring due to a nonspecific reaction, discoloration due to degradation of a reagent with time, adhesion of dust or the like, may occur. According to visual observation, it is possible to discriminate such abnormal coloring from normal coloring. However, the immunoassay analyzer erroneously may detect such abnormal coloring.

PRIOR ART DOCUMENTS

Patent Documents

[Patent Document 1] JP 2005-24323 A

SUMMARY OF THE INVENTION

Problem to be Solved by the Invention

With the foregoing in mind, it is an object of the present invention to provide an immunoassay analyzer and an immunoassay method, each capable of discriminating between normal coloring due to a specific immunoreaction and abnormal coloring due to a cause other than the specific immunoreaction in a measurement region of sample analysis tool.

Means for Solving Problem

The immunoassay analyzer of the present invention is an immunoassay analyzer for determining the presence or absence of a substance to be detected in a sample by detecting color change due to a specific immunoreaction in a sample analysis tool. The immunoassay analyzer includes: an optical detection unit for detecting color change in the sample analysis tool; and a determination unit for determining the presence or absence of the substance to be detected based on information from the optical detection unit. The optical detection unit includes an optical signal measurement unit for measuring an optical signal at each of two or more different wavelengths including a main wavelength for detecting the color change due to the specific immunoreaction and a sub-wavelength other than the main wavelength. The determination unit includes a discrimination unit for comparing the respective optical signals at the two or more different wavelengths, including the optical signal at the main wavelength and discriminating between the color change due to the specific immunoreaction and color change due to a cause other than the specific immunoreaction based on a comparison criterion determined previously. In the determination unit, when no color change in the sample analysis tool is detected, it is determined that the sample is negative regarding that the substance to be detected is not present. When color change in the sample analysis tool is detected, it is determined that the sample is positive regarding that the substance to be detected is present in the case where the discrimination unit determines that the detected color change is due to the specific immunoreaction, and it is determined that the determination is invalid in the case where the discrimination unit determines that the detected color change is due to a cause other than the specific immunoreaction.

The immunoassay method of the present invention is an immunoassay method for determining the presence or absence of a substance to be detected in a sample by detecting color change due to a specific immunoreaction in a sample analysis tool. The immunoassay method includes: an optical detection step of detecting color change in the sample analysis tool; and a determination step of determining the presence or absence of the substance to be detected based on information obtained in the optical detection step. The optical detection step includes an optical signal measurement step of measuring an optical signal at each of two or more different wavelengths including a main wavelength for detecting the color change due to the specific immunoreaction and a sub-wavelength other than the main wavelength. The determination step includes a discrimination step of comparing the respective optical signals at the two or more different wavelengths, including the optical signal at the main wavelength and discriminating between the color change due to the specific immunoreaction and color change due to a cause other than the specific immunoreaction based on a comparison criterion determined previously. In the determination step, when no color change in the sample analysis tool is detected, it is determined that the sample is negative regarding that the substance to be detected is not present. When color change in the sample analysis tool is detected, it is determined that the sample is positive regarding that the substance to be detected is present in the case where the discrimination unit determines that the detected color change is due to the specific immunoreaction, and it is determined that the determination is invalid in the case where the discrimination unit determines that the detected color change is due to a cause other than the specific immunoreaction.

Effects of the Invention

According to the present invention, it is possible to discriminate between normal coloring due to a specific immunoreaction and abnormal coloring due to a cause other than the specific immunoreaction easily by measuring, in addition to an absorbance at a main wavelength for detecting color change due to the specific immunoreaction, an absorbance at a sub-wavelength other than the main wavelength and carrying out determination based on a comparison criterion. Thus, the present invention can avoid an erroneous determination based on abnormal coloring such as coloring due to a cause other than immunoreactions, e.g., coloring due to a nonspecific reaction, adhesion of dust, or the like, thus achieving high analysis accuracy. Moreover, the absorbance measurement at two or more wavelengths and the determination based on the result thereof can be carried out easily, so that the analyzer of the present invention does not need have a particularly complicated configuration.

MODE FOR CARRYING OUT THE INVENTION

Figure 1A:
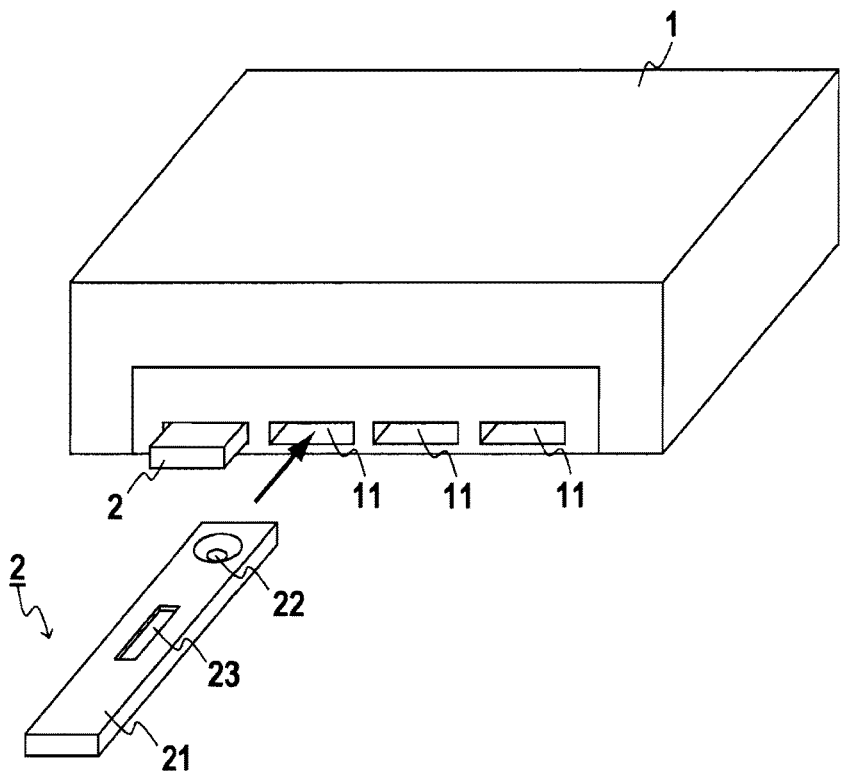
FIG. 1A is a perspective view showing an example of an immunoassay analyzer of the present invention and an example of a sample analysis tool used for the immunoassay analyzer.

In the present invention, as described above, by detecting the color change in the sample analysis tool, either one of "negative", "positive", and "invalid determination" is given as a determination result. The "negative" is the determination result that the substance to be detected is not present in the sample, for example. The "positive" is the determination result that the substance to be detected is present in the sample, for example. The "invalid determination" is the determination result that the determination is regarded as invalid because color change due to a cause other than the specific immunoreaction of the substance to be detected is detected, for example. In the present invention, the positive determination can be ranked on a scale of, for example, 1+, 2+, 3+, and the like, depending on the degree of the color change (e.g., the color intensity or the like), for example. Indication of the rank is not limited to 1+ and the like described above. For example, it may be indication representing any other quantitative or semiquantitative determination, or the like, and is not particularly limited. In the present invention, color change due to the specific immunoreaction refers to, for example, color change due to a specific immunoreaction with a target substance to be detected.

<Immunoassay Analyzer>

The immunoassay analyzer of the present invention is, as described above, an immunoassay analyzer for determining the presence or absence of a substance to be detected in a sample by detecting color change due to a specific immunoreaction in a sample analysis tool. The immunoassay analyzer includes: an optical detection unit for detecting color change in the sample analysis tool; and a determination unit for determining the presence or absence of the substance to be detected based on information from the optical detection unit. The optical detection unit includes an optical signal measurement unit for measuring an optical signal at each of two or more different wavelengths including a main wavelength for detecting the color change due to the specific immunoreaction and a sub-wavelength other than the main wavelength. The determination unit includes a discrimination unit for comparing the respective optical signals at the two or more different wavelengths, including the optical signal at the main wavelength and discriminating between the color change due to the specific immunoreaction and color change due to a cause other than the specific immunoreaction based on a comparison criterion determined previously. In the determination unit, when no color change in the sample analysis tool is detected, it is determined that the sample is negative regarding that the substance to be detected is not present. When color change in the sample analysis tool is detected, it is determined that the sample is positive regarding that the substance to be detected is present in the case where the discrimination unit determines that the detected color change is due to the specific immunoreaction, and it is determined that the determination is invalid in the case where the discrimination unit determines that the detected color change is due to a cause other than the specific immunoreaction.

In the present invention, for example, the number of the kinds of substance to be detected detectable by one sample analysis tool may be one, or may be two or more. In the latter case, for example, a main wavelength for detecting color change due to a specific immunoreaction is set for each of the objects to be detected.

The number of sub-wavelengths to be set with respect to one main wavelength may be one or may be two or more, for example, and is not particularly limited. The former case is an embodiment where analysis is carried out using two wavelengths, and in the determination unit, an optical signal at the main wavelength is compared with an optical signal at the sub-wavelength. The latter case is an embodiment where, for example, analysis is carried out using three or more wavelengths, and an optical signal at the main wavelength may be compared with any one of optical signals at the sub-wavelengths, or the optical signal at the main wavelength may be compared with each of the optical signals at the sub-wavelengths. When there are two or more kinds of substance to be detected as described above, the number of sub-wavelengths to be set with respect to each main wavelength may be one or may be two or more, for example, as described above. Furthermore, with respect to the respective main wavelengths, for example, the same sub-wavelength may be set or different sub-wavelengths may be set. Still further, for example, a main wavelength for each substance to be detected may be used as a sub-wavelength for another substance to be detected. In particular, for example, when it is intended to determine which of the objects to be detected is contained in a sample, it is preferable that a main wavelength for each substance to be detected is used as a sub-wavelength for another substance to be detected. With this configuration, it becomes possible to more accurately determine which of the plurality of objects to be detected is contained in the sample.

The kind of the optical signal is not particularly limited. It can be, for example, an absorbance, a reflectance, a transmittance, or the like. Generally, it is possible to calculate a reflectance from an absorbance, a transmittance from an absorbance, an absorbance from a reflectance, and an absorbance from a transmittance. Thus, in the present invention, it can be said that, for example, from a measured value of any one of them, the others can be measured indirectly.

The immunoassay analyzer of the present invention may be configured so that, in the discrimination unit, the comparison criterion is a standard value for a magnitude relationship between the optical signal at the main wavelength and the optical signal at the sub-wavelength, the optical signal at the main wavelength is compared with the optical signal at the sub-wavelength based on the standard value for the magnitude relationship, and the color change due to the specific immunoreaction and the color change due to a cause other than the specific immunoreaction are discriminated based on a result of the comparison. For example, when two or more sub-wavelengths are set with respect to one main wavelength, two or more standard values indicating the magnitude relationship between an optical signal at the main wavelength and each of optical signals at the sub-wavelengths may be used.

Examples of the comparison between the optical signal at the main wavelength and the optical signal at the sub-wavelength include comparison using a ratio and comparison using a difference.

First, an example of the comparison in the case where the optical signal is an absorbance will be described. In the comparison using the ratio, for example, in the discrimination unit, an absorbance at the main wavelength is compared with an absorbance at the sub-wavelength by determining a ratio (R) between the absorbance (A) at the main wavelength and the absorbance (B) at the sub-wavelength, defined by the following equation (1). The standard value for the magnitude relationship is a standard value (Rs) for the ratio. When a calculated value (R) of the ratio is equal to or larger than the standard value (Rs) for the ratio, it is determined that the sample is positive, and when the calculated value (R) of the ratio is smaller than the standard value (Rs) for the ratio, it is determined that the determination is invalid. Alternatively, when the calculated value (R) of the ratio is larger than the standard value (Rs) for the ratio, it may be determined that the sample is positive, and when the calculated value (R) of the ratio is equal to or smaller than the standard value (Rs) for the ratio, it may be determined that the determination is invalid.

$$R=A/B \tag{1}$$

In the comparison using the ratio, for example, the ratio may be a calculated value (R') of the ratio defined by the following equation (1'), and the standard value for the magnitude relationship may be a standard value (Rs') for the ratio. In this case, when the calculated value (R') of the ratio is equal to or smaller than the standard value (Rs') for the ratio, it is determined that the sample is positive, and when the calculated value (R') of the ratio is larger than the standard value (Rs') for the ratio, it is determined that the determination is invalid. Alternatively, when the calculated value (R') of the ratio is smaller than the standard value (Rs') for the ratio, it may be determines that the sample is positive, and when the ratio (R') is equal to or larger than the standard value (Rs'), it may be determined that the determination is invalid.

$$R'=B/A \tag{1'}$$

In the comparison using the difference, for example, in the discrimination unit, an absorbance at the main wavelength is compared with an absorbance at the sub-wavelength by determining a difference (D) between the absorbance (A) at the main wavelength and the absorbance (B) at the sub-wavelength, defined by the following equation (2). The standard value for the magnitude relationship is a standard value (Ds) for the difference. When a calculated value (D) of the difference is equal to or larger than the standard value (Ds) for the difference, it is determined that the sample is positive, and when the calculated value (D) of the difference is smaller than the standard value (Ds) for the difference, it is determined that the determination is invalid. Alternatively, when the difference (D) is larger than the standard value (Ds), it may be determined that the sample is positive, and when the difference (D) is equal to or smaller than the standard value (Ds), it may be determined that the determination is invalid.

$$D=A-B \tag{2}$$

In the comparison using the difference, for example, the difference may be a calculated value (D') of the difference defined by the following equation (2'), and the standard value for the magnitude relationship may be a standard value (Ds') for the difference. In this case, when the calculated value (D') of the difference is equal to or smaller than the standard value (Ds') for the difference, it is determined that the sample is positive, and when the calculated value (D') of the difference is larger than the standard value (Ds') for the difference, it is determined that the determination is invalid. Alternatively, when the difference (D') is smaller than the standard value (Ds'), it may be determined that the sample is positive, and when the difference (D') is equal to or larger than the standard value (Ds'), it may be determined that the determination is invalid.

$$D'=B-A \tag{2'}$$

Next, an example of the comparison in the case where the optical signal is a reflectance will be described. In the comparison using the ratio, for example, in the discrimination unit, a reflectance at the main wavelength is compared with a reflectance at the sub-wavelength by determining a ratio (Rr) between the reflectance (P) at the main wavelength and the reflectance (Q) at the sub-wavelength, defined by the following equation (3). The standard value for the magnitude relationship is a standard value (Rrs) for the ratio. When a calculated value (Rr) of the ratio is equal to or smaller than the standard value (Rrs) for the ratio, it is determined that the sample is positive, and when the calculated value (Rr) of the ratio is larger than the standard value (Rrs) for the ratio, it is determined that the determination is invalid. Alternatively, when the calculated value (Rr) is smaller than the standard value (Rrs) for the ratio, it may be determined that the sample is positive, and when the calculated value (Rr) of the ratio is equal to or larger than the standard value (Rrs) for the ratio, it may be determined that the determination is invalid.

$$Rr=P/Q \qquad (3)$$

In the comparison using the ratio, for example, the ratio may be a calculated value (Rr') of the ratio between the reflectance (P) at the main wavelength and the reflectance (Q) at the sub-wavelength, defined by the following equation (3'), and the standard value for the magnitude relationship may be a standard value (Rrs') for the ratio. In this case, when the calculated value (Rr') of the ratio is equal to or larger than the standard value (Rrs') for the ratio, it is determined that the sample is positive, and when the calculated value (Rr') of the ratio is smaller than the standard value (Rrs') for the ratio, it is determined that the determination is invalid. Alternatively, when the calculated value (Rr') of the ratio is larger than the standard value (Rrs') for the ratio, it may be determined that the sample is positive, and when the calculated value (Rr') of the ratio is equal to or smaller than the standard value (Rrs') for the ratio, it may be determined that the determination is invalid.

$$Rr'=Q/P \qquad (3')$$

In the comparison using the difference, in the discrimination unit, a reflectance at the main wavelength is compared with a reflectance at the sub-wavelength are compared by determining a difference (Dr) between the reflectance (P) at the main wavelength and the reflectance (Q) at the sub-wavelength, defined by the following equation (4). The standard value for the magnitude relationship is a standard value (Drs) for the difference. When a calculated value (Dr) of the difference is equal to or smaller than the standard value (Drs) for the difference, it is determined that the sample is positive, and when the calculated value (Dr) of the difference is larger than the standard value (Drs) for the difference, it is determined that the determination is invalid. Alternatively, when the calculated value (Dr) of the difference is smaller than the standard value (Drs) for the difference, it may be determined that the sample is positive, and when the calculated value (Dr) of the difference is equal to or larger than the standard value (Drs) for the difference, it may be determined that the determination is invalid.

$$Dr=P-Q \qquad (4)$$

In the comparison using the difference, for example, the difference may be a difference (Dr') between the reflectance (P) at the main wavelength and the reflectance (Q) at the sub-wavelength, defined by the following equation (4'), and the standard value for the magnitude relationship may be a standard value (Drs') for the difference. In this case, when the calculated value (Dr') of the difference is equal to or larger than the standard value (Drs') for the difference, it is determined that the sample is positive, and when the calculated value (Dr') of the difference is smaller than the standard value (Drs') for the difference, it is determined that the determination is invalid. Alternatively, when the calculated value (Dr') of the difference is larger than the standard value (Drs') for the difference, it may be determined that the sample is positive, and when the calculated value (Dr') of the difference is equal to or smaller than the standard value (Drs') for the difference, it may be determined that the determination is invalid. Note here that the same equation and the determination method for the reflectance also are applicable to the transmittance, for example.

$$Dr'=Q-P \qquad (4')$$

The setting of the standard value for the ratio and difference is not particularly limited. For example, data regarding the optical signal at the main wavelength and the optical signal at the sub-wavelength in the case of the normal coloring due to a specific immunoreaction and the case of the abnormal coloring due to a cause other than the specific immunoreaction may be collected beforehand, and the standard value may be set based on the data.

In the determination unit, an example of the case where color change in the sample analysis tool is not detected is the case where an optical signal at the main wavelength cannot be detected (for example, the concentration of the substance to be detected is lower than the detection limit). Furthermore, in the determination unit, it may be determined that the sample is negative when the optical signal at the main wavelength indicates that no color change of the sample analysis tool is detected based on a previously determined standard, and the discrimination unit may discriminate whether the detected color change is due to the specific immunoreaction or a cause other than the specific immunoreaction.

The latter case will be illustrated in the following. In the case where the optical signal is an absorbance, for example, it is preferable that, in the determination unit, when the absorbance at the main wavelength is smaller than a previously determined standard value (or equal to or smaller than the standard value), it is determined that the sample is negative, and when the absorbance at the main wavelength is equal to or larger than the standard value (or larger than the standard value), the discrimination unit discriminates whether the detected color change is due to the specific immunoreaction or a cause other than the specific immunoreaction. Furthermore, when the optical signal is a reflectance or a transmittance, for example, it is preferable that, in the determination unit, when the reflectance or transmittance at the main wavelength is larger than a previously determined standard value (equal to or larger than the standard value), it is determined that the sample is negative, and when the reflectance or transmittance at the main wavelength is equal to or smaller than the standard value (or smaller than the standard value), the discrimination unit discriminates whether the detected color change is due to the specific immunoreaction or a cause other than the specific immunoreaction. The setting of the standard value is not particularly limited. For example, data regarding the optical signal at the main wavelength in the case of the normal coloring due to a specific immunoreaction and in the case where coloring has not occurred may be collected beforehand, and the standard value may be set based on the data. Specifically, for example, with respect to a sample analysis tool colored normally and a sample analysis tool not colored, data regarding the optical signal at the main wavelength may be collected in the same manner by means of visual observation, and the standard value may be set based on the data. Alternatively, for example, a standard solution of a target substance to be detected may be prepared so as to have a detection limit concentration and an immunoreaction may be caused using a sample analysis tool. Then, data regarding the optical signal at the main wavelength may be collected, and the standard value may be set based on the data.

The wavelength difference between the main wavelength and the sub-wavelength preferably is at least 10 nm, more preferably at least 20 nm, for example. The wavelength difference is, for example, in the range from 10 nm to 500 nm, more preferably from 20 nm to 300 nm, and still more preferably from 50 nm to 300 nm.

In the immunoassay analyzer of the present invention, the discrimination unit may further discriminates whether the color change due to a cause other than the specific immunoreaction is due to a nonspecific reaction or a cause other than immunoreactions. The color change due to a nonspecific reaction refers to, for example, color change due to a non-specific immunoreaction caused by a substance other than the substance to be detected. The color change due to a cause other than immunoreactions is color change that is not caused by any immunoreactions, and examples thereof include color change due to the degradation of a reagent or a component used in the sample analysis tool, color change due to adhesion of a foreign substance such as dust or the like, and color change due to a flaw or dirt.

In the discrimination unit of the immunoassay analyzer of the present invention, a method for discriminating whether the color change due to a cause other than the specific immunoreaction is due to a nonspecific reaction or due to dust or the like may be, for example, the following method. This method is an example of a method for detecting which of a first substance to be detected and a second substance to be detected different from the first object is contained in the sample. The method uses two different labeling substances, and carries out the measurement using three measurement wavelengths. First, first labeled antibodies obtained by labeling antibodies against the first substance to be detected with a first labeling substance and second labeled antibodies obtained by labeling antibodies against the second substance to be detected with a second labeling substance are provided. As the first and second labeling substances, labeling substances having absorption peaks different from each other are selected. Then, on a porous membrane of a sample analysis tool, the antibodies against the first substance to be detected and the antibodies against the second substance to be detected are immobilized separately, thus forming measurement regions. On one end side of the porous membrane, the two kinds of labeled antibodies are disposed. A sample is applied thereto, and the two kinds of labeled antibodies and the sample are moved to the measurement regions utilizing a capillary phenomenon or the like. Then, the measurement regions are irradiated with light having a main wavelength for detecting the first labeling substance, light having a main wavelength for detecting the second labeling substance, and light having a wavelength (a third wavelength) that is different from the main wavelengths for the two labeling substances, and an absorbance in the region on which the antibodies against the first substance to be detected are immobilized and an absorbance in the region on which the antibodies against the second substance to be detected are immobilized are measured. The main wavelength for the first labeling substance and the main wavelength for the second labeling substance are set in the vicinity of the wavelengths at which the respective absorption peaks are shown. In this embodiment, the main wavelength for the second labeling substance and the third wavelength serve as sub-wavelengths for the first labeling substance, and the main wavelength for the first labeling substance and the third wavelength serve as sub-wavelengths for the second labeling substance. Next, determination is carried out based on the respective absorbances in the following manner. The absorbance at the main wavelength for the first labeling substance (absorbance a), the absorbance at the main wavelength for the second labeling substance (absorbance b), and the absorbance at the third wavelength (absorbance c) are all small, it is determined that the sample is "negative" for both the first and second objects to be detected. When the absorbance a is large and the absorbances b and c are small, it is regarded that the color change has been caused by the specific immunoreaction with the first substance to be detected, so that it is determined that the sample is "positive" for the first substance to be detected and "negative" for the second substance to be detected. When the absorbance b is large and the absorbances a and c are small, it is regarded that the color change has been caused by the specific immunoreaction with the second substance to be detected, so that it is determined that the sample is "negative" for the first substance to be detected and "positive" for the second substance to be detected. When the absorbances a and b are large and the absorbance c is small, it is regarded that the color change has been caused by the binding of either the first labeled antibodies and the second labeled antibodies to the corresponding measurement region through the nonspecific reaction, so that it is determined that "determination is invalid" because the color change is due to the nonspecific reaction. When all the absorbances a, b, and c are large, it is regarded that the color change has been caused by dust or the like, so that it is determined that "determination is invalid" because the color change is due to the dust or the like. Thus, in the method, based on the magnitude relationship among the absorbances a, b, and c, it is possible to carry out the determination while discriminating among the color change due to a specific immunoreaction, the color change due to a nonspecific reaction, and the color change due to dust or the like. Note here that this method is shown merely for an illustrative purpose and by no means limits the present invention. Furthermore, it is possible to use, for example, labeled antigens and immobilized antigens instead of the labeled antibodies and the immobilized antibodies as appropriate depending on the kind of the substance to be detected.

The immunoassay analyzer of the present invention may be configured so that; the sample analysis tool includes a measurement region, an immobilized antibody or immobilized antigen (hereinafter also referred to as "immobilized antibody or the like") that can bind to the substance to be detected and is immobilized on the measurement region; the sample and a labeled antibody or the like that can bind to the substance to be detected and is labeled with a label identifiable through color change are introduced into the measurement region of the sample analysis tool; when the substance to be detected is present in the sample, the labeled antibody or the like binds to the immobilized antibody or the like via the substance to be detected to form a complex, whereby color change is caused in the measurement region by the label; and the color change in the measurement region is detected by the optical detection unit. The present embodiment may be, as will be described later, an embodiment where two kinds of antibodies, namely, an immobilized antibody and a labeled antibody are used, an embodiment where an immobilized antigen and a labeled antibody are used, an embodiment where an immobilized antibody and a labeled antigen are used, or an embodiment where two kinds of antigens, namely, an immobilized antigen and a labeled antigen are used. The embodiment where two kinds of reagents, namely, immobilized antibody or antigen and labeled antibody or antigen are used can be divided roughly into, for example, a lateral-flow type and a flow-through type depending on the configuration of the sample analysis tool. Preferably, the sample analysis tool includes a channel because the sample and the reagents such as the antibody and the like can move along the channel, for example. The channel may be, for example, a pore structure in a porous membrane or a groove provided on a substrate. Preferably, the sample analysis tool includes, for example, a porous membrane including the measurement region.

In the present invention, the label used in the labeled antibody and the labeled antigen may be, for example, a colored insoluble carrier particle and the color change may be coloring of the measurement region caused by the formation of the complex containing the colored insoluble carrier particle. Alternatively, the label may be, for example, an enzyme, and the color change may be coloring of the measurement region resulting from coloring of a substrate through an enzyme reaction of the substrate and the enzyme contained in the complex.

In the present invention, for example, there may be a plurality of kinds of objects to be detected, a plurality of kinds of immobilized antibodies or the like corresponding to the respective objects to be detected may be immobilized in the measurement region, and the plurality of kinds of labeled antibodies or labeled antigens corresponding to the respective objects to be detected may be introduced into the measurement region.

In the immunoassay analyzer of the present invention, the optical signal measurement unit is not particularly limited, and can be determined as appropriate depending on the kind of an optical signal to be measured, for example. When the optical signal is the absorbance, the immunoassay analyzer preferably includes an absorbance measurement unit. When the optical signal is the reflectance, the immunoassay analyzer preferably includes a reflectance measurement unit. When the optical signal is the transmittance, the immunoassay analyzer preferably includes a transmittance measurement unit. Furthermore, the optical signal measurement unit may have, for example, one, two, or all of the units selected from the group consisting of the absorbance measurement unit, the reflectance measurement unit, and the transmittance measurement unit.

Next, the present invention will be described in detail by way of examples.

In the present invention, the sample is not particularly limited as long as it contains a specimen or the like, for example. The sample may be prepared by, for example, treating the specimen. The treatment is not particularly limited, and examples thereof include an extraction treatment, a dilution treatment, and a filtration treatment. In the case of the extraction treatment, for example, the sample may be prepared by adding the specimen to a treatment solution and extracting antigens or antibodies in the specimen. It is preferable that the specimen is in the form of liquid, for example. However, the specimen is not limited thereto, and may be in the form of solid, for example. When the specimen is in the form of solid, for example, a solution obtained by dissolving, suspending, or dispersing the specimen in the treatment solution may be used as a sample, or a solution obtained by further filtering the thus-obtained solution may be used as a sample. The treatment solutions to be used in the above-described various treatments are not particularly limited, and examples thereof include buffers such as a Tris buffer, a phosphate buffer, an acetic acid buffer, and a boric acid buffer. To the above-described various treatment solutions, a surfactant, a stabilizer, an antibacterial agent, etc. may be added as appropriate. The filtration treatment is not particularly limited, and may be carried out using a membrane filter or the like, for example. The specimen is not particularly limited, and examples thereof include: biological specimens such as nasal aspirate, nasal lavage fluid, nasal swab, nasal secretion, throat swab, oral rinse, saliva, whole blood, serum, plasma, feces, urine, and cerebrospinal fluid; foods such as food substances like animals and plants, and processed foods; and water collected from rivers in environmental inspection.

In the present invention, examples of the substance to be detected include biogenic substances etc. including pathogen antigens, antibodies, cancer markers, and hormones, such as influenza A viruses, influenza B viruses, influenza C viruses, adenoviruses, RS viruses, coronaviruses, astroviruses, noroviruses, measles viruses, rotaviruses, human immunodeficiency viruses (HIV), human T-cell leukemia viruses (HTLV-1), hepatitis B viruses (HBV), hepatitis C viruses (HCV), herpesviruses, *Mycoplasma, Treponema pallidum, Chlamydia trachomatis*, tubercle bacilli, coliform bacteria, group A hemolytic streptococci (group A streptococci), group B hemolytic streptococci (group B streptococci), *Streptococcus pneumoniae, staphylococci*, MRSA, *Legionella, enterohemorrhagic Escherichia coli* O157, verotoxin, *Salmonella, Clostridium difficile, Helicobacter pylori*, CRP, HBs antigens, HBs antibodies, HBc antigens, HBc antibodies, HBe antigens, HBe antibodies, prostate-specific antigens (PSA), human chorionic gonadotrophin (hCG), luteinizing hormone (LH), troponin T, troponin I, myoglobin, D-dimer, fecal hemoglobin, hemoglobin A1c, and IgE antibodies. However, the substance to be detected is not limited thereto. Examples of the substance to be detected further include residual agricultural chemicals, environment hormones, and allergic substances in foods, and the substance to be detected is not particularly limited. In the present invention, there may be one kind of substance to be detected, or alternatively, two or more kinds of objects to be detected may be combined.

In the present invention, the kind of a specific immunoreaction causing color change is not particularly limited, and conventionally known immunoreactions may be employed.

Specifically, given as a first example is a method in which antibodies that specifically react with a substance to be detected are used as a detection reagent. Preferably, immobilized antibodies immobilized on a measurement region of a sample analysis tool and labeled antibodies having a label bound thereto, for example, are used as the antibodies. When such antibodies are used, for example, if the substance to be detected is present in the sample, complexes are formed on the measurement region of the sample analysis tool by the bonding of the substance to be detected with the immobilized antibodies and the labeled antibodies through an immunoreaction.

Furthermore, given as a second example is a method in which antigens with which the substance to be detected specifically reacts and antibodies that specifically react with the substance to be detected are used as a detection reagent. The antigens preferably are, for example, immobilized antigens immobilized on the measurement region of the sample analysis tool and the antibodies preferably are, for example, labeled antibodies having a label bound thereto. When such a detection reagent is used, for example, if the substance to be detected is present in the sample, complexes are formed on the measurement region of the sample analysis tool by the bonding of the substance to be detected with the immobilized antigens and the labeled antibodies through an immunoreaction.

Still further, given as a third example is a method in which antigens with which the substance to be detected specifically react are used as a detection reagent. Preferably, immobilized antigens immobilized on the measurement region of the sample analysis tool and labeled antigens having a label bound thereto, for example, are used as the antigens. When such a detection reagent is used, for example, if the substance to be detected is present in the sample, complexes are formed on the measurement region of the sample analysis tool by the bonding of the substance to be detected with the immobilized antigens and the labeled antigens through an immunoreaction.

With respect to the complexes formed through the immunoreaction as described above, color change may be measured depending on the kind of the label in the labeled antibodies or the labeled antigens as will described later.

In the present invention, the labeled antibodies or the labeled antigens are not particularly limited, and, for example, it may be antibodies or antigens to which colored insoluble carrier particles are bound as a label, or may be antibodies or antigens to which an enzyme is bound as a label.

In the present invention, the colored insoluble carrier particles are not particularly limited, and examples thereof include colored latex particles, metal colloid particles, colored polymethyl methacrylate particles, colored polylactic acid particles, colored porous glass particles, colored silica particles, colored agarose particles, and colored dextran particles. The colored latex particles are not particularly limited, and examples thereof include blue latex particles and red latex particles. The metal colloid particles are not particularly limited, and examples thereof include gold colloid particles and platinum colloid particles. The average particle diameter of the colored insoluble carrier particles is not particularly limited. In the case of the colored latex particles, the average particle diameter is, for example, in the range from 0.05 µm to 5 µm, preferably from 0.1 µm to 1 µm. In the case of the metal colloid particles, the average particle diameter is, for example, in the range from 2 nm to 100 nm, preferably from 10 nm to 50 nm. In the present invention, in the case where there are two or more kinds of objects to be detected, it is preferable to use, for example, two or more kinds of colored insoluble carrier particles that are colored differently. When using the two or more kinds of differently colored insoluble carrier particles, the wavelength difference between the absorption peaks of the respective kinds of particles preferably is, for example, at least 10 nm, more preferably at least 20 nm. The wavelength difference is, for example, in the range from 10 nm to 500 nm, more preferably from 20 nm to 300 nm, and still more preferably from 50 nm to 300 nm. Preferably, a wavelength at or in the vicinity of the absorption peak of each kind of colored insoluble carrier particles is set to a main wavelength for detecting color change by the colored insoluble carrier particles. Furthermore, for a certain kind of colored insoluble carrier particles, as described above, a main wavelength for detecting color change by a different kind of colored insoluble carrier particles may be set as a sub-wavelength therefor.

In the present invention, the enzyme is not particularly limited as long as it causes a substrate to develop color when it reacts with the substrate. Examples of the enzyme include peroxidase, alkaline phosphatase, and β-D-galactosidase.

In the present invention, the substrate is not particularly limited as long as it develops color when it reacts with the enzyme. Examples of the substrate include 2,2'-azino-bis(3-ethylbenzothiazoline-6-sulfonic acid) (ABTS), 3,3',5,5'-tetramethylbenzidine (TMB), diaminobenzidine (DAB), 5-bromo-4-chloro-3-indolylphosphate (BCIP), 4-methylumbelliferyl-β-D-galactoside (4MUG), and 3-(2'-spiroadamantane)-4-methoxy-4-(3"-β-D-galactopyranosyl)phenyl-1,2-dioxetane (AMGPD).

In the present invention, when there are two or more kinds of objects to be detected, it is preferable that color developed through the reaction of the enzyme with the substrate varies from one substance to be detected to another, for example. In this case, the enzyme and the substrate for each substance to be detected preferably are selected so that color developed by the combination thereof when they react with each other varies from one substance to be detected to another, for example. The wavelength difference between the absorption peaks of the respective colors may be, for example, in the above-described range. Preferably, a wavelength at or in the vicinity of the absorption peak of each coloring is set to a main wavelength for detecting color change by the coloring. Furthermore, for certain coloring, the main wavelength for detecting color change by the coloring may be set as a sub-wavelength therefor.

In the present invention, antibodies used as the above-described labeled antibodies are not particularly limited as long as they can bind to the substance to be detected. Examples thereof include antibodies that can bind to the various antigens described above as examples of the substance to be detected and antibodies that can bind to various antibodies. The kind of the antibodies is not particularly limited, and examples thereof include IgG, IgA, IgM, IgD, IgE, and IgY. The antibodies may be, for example, antibody fragments such as immunoglobulin molecules, Fab, Fab', or F(ab')$_2$, or the like, and are not particularly limited. Moreover, the antibodies may be produced from serum derived from, for example, a mammal such as a mouse, a rabbit, a goat, or a sheep, or a bird such as a chicken by a conventionally known method, or any of various kinds of commercially available antibody may be used, and are not particularly limited. Still further, as the antibodies, either of polyclonal antibodies and monoclonal antibodies may be used, for example, and they can be set as appropriate depending on the substance to be detected or the like. In the present invention, examples of the antibodies used as the above-described immobilized antibodies include, as in the case of the labeled antibodies, antibodies that can bind to the substance to be detected. The kind of the immobilized antibodies or a method for preparing the immobilized antibodies are the same as those described for the labeled antibodies, for example.

In the present invention, antigens used as the above-described labeled antigens are not particularly limited as long as they can bind to the substance to be detected. Examples thereof include antigens that can bind to the various antibodies described above as examples of the substance to be detected. Furthermore, in the present invention, antigens used as the above-described immobilized antigens are not particularly limited. Examples thereof include, as in the case of the labeled antigens, antigens that can bind to the substance to be detected. In the present invention, methods for producing the labeled antigens and the immobilized antigens may be, for example, conventionally known methods and the like, and are not particularly limited.

In the present invention, the range of the main wavelength and the range of the sub-wavelength are not particularly limited, and can be determined as appropriate depending on color change to be detected, for example. As a specific example, when the color change due to a specific immunoreaction is blue, the main wavelength may be set, for example, in the range from 600 to 660 nm (e.g., 610 nm) and the sub-wavelength may be set, for example, in the range from 500 to 550 nm (e.g., 525 nm). As another specific example, when the color change due to a specific immunoreaction is red, the main wavelength may be set, for example, in the range from 500 to 550 nm (e.g., 525 nm) and the sub-wavelength may be set, for example, in the range from 600 to 660 nm (e.g., 610 nm).

Next, the immunoassay analyzer of the present invention will be described with reference to an example in which a reflectance is measured as an optical signal. It is to be noted, however, the immunoassay analyzer of the present invention is not limited to the following example.

Figure 1B:
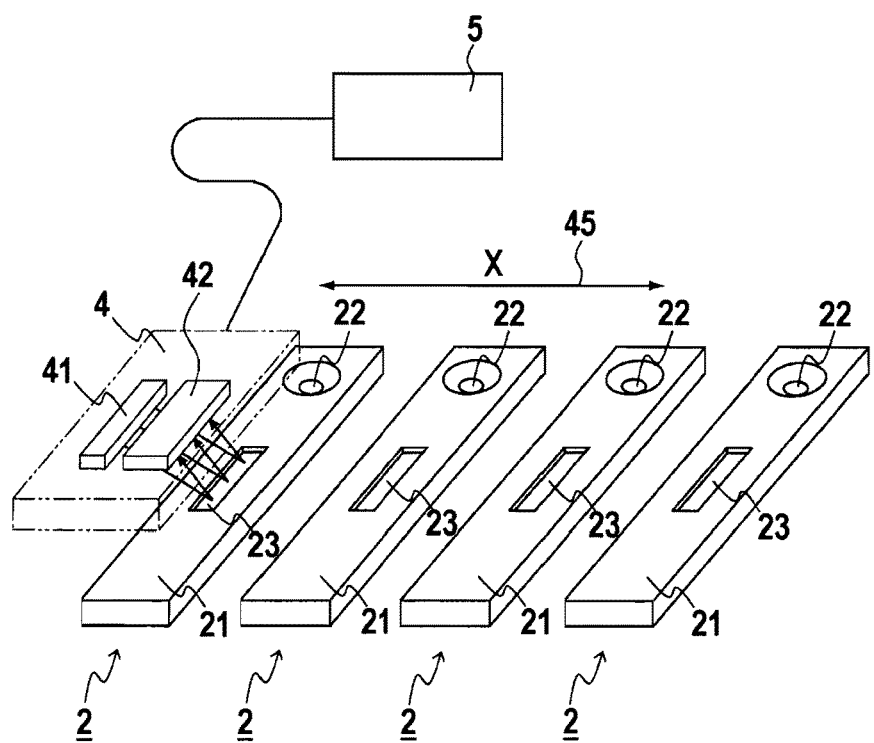
FIG. 1B is a schematic view showing the internal structure of the immunoassay analyzer shown in FIG. 1A.

FIG. 1 shows an immunoassay analyzer of the present example. FIG. 1A is a perspective view of an immunoassay analyzer of the present example and a sample analysis tool used in the immunoassay analyzer. FIG. 1B is a schematic view showing the internal structure of the immunoassay analyzer shown in FIG. 1A. In FIGS. 1A and 1B, common components are given the same reference numerals. As shown in FIG. 1A, in the immunoassay analyzer 1 of the present example, a plurality of insertion slots 11 to which sample analysis tools 2 are inserted are formed on the front side of a box-shaped analyzer main body. The sample analysis tool 2 is configured so that a test piece (not shown in FIG. 1) is contained in a case body 21. On an upper surface of the case body 21, a sample hole 22 through which a sample is supplied and a measurement window 23 from which measurement regions of the test piece are exposed are formed. The configuration of the test piece will be described later.

As shown in FIG. 1B, the immunoassay analyzer 1 of the present example includes a measurement unit 4 and a control and analysis portion 5, and they serve as an optical detection unit including an optical signal measurement unit and a determination unit, respectively. The measurement unit 4 includes a light source portion 41 and a light receiving portion 42, and can move in an X direction 45. In the present example, the light source portion 41 and the light receiving portion 42 are disposed above the sample analysis tool 2 inserted into the immunoassay analyzer 1, and reflected light of irradiation light emitted from the light source portion 41 can be measured by the light receiving portion 42. The light source portion 41 includes, for example, a light emitting diode (LED), a semiconductor laser diode (LD), or the like. The light receiving portion 42 includes, for example, a photodiode, a photomultiplier tube, a CCD image sensor, or the like. In the present example, the light receiving portion 42 measures reflected lights of the irradiation lights having two wavelengths alternately at a time difference. The control and analysis portion 5 has a control unit for controlling light emission and light reception in the light source portion 41 and the light receiving portion 42 of the measurement unit 4 and a determination unit for determining whether the sample is positive, negative, or the like by calculating reflectances based on the measured reflected lights. In the present example, the determination unit includes, for example, a CPU, a memory, an input terminal, and an output terminal. Examples of the input terminal include a keyboard and a touch panel. Examples of the output terminal include a display and a printer. The whole of the control and analysis portion 5 may be disposed in the main body of the analyzer according to the present example, or the whole or a part of the control and analysis portion 5 may be disposed outside the analyzer main body. For example, the control unit may be provided in a personal computer (PC). Furthermore, in a CPU, for example, determination or discrimination as to whether the sample is positive or negative or determination is invalid is carried out by the determination unit. The above-described various standard values for determination to be used in the determination unit may be stored in a memory previously and referred to at the time of making determination, or may be inputted to the CPU through an input means for reference, for example.

Figure 2A:
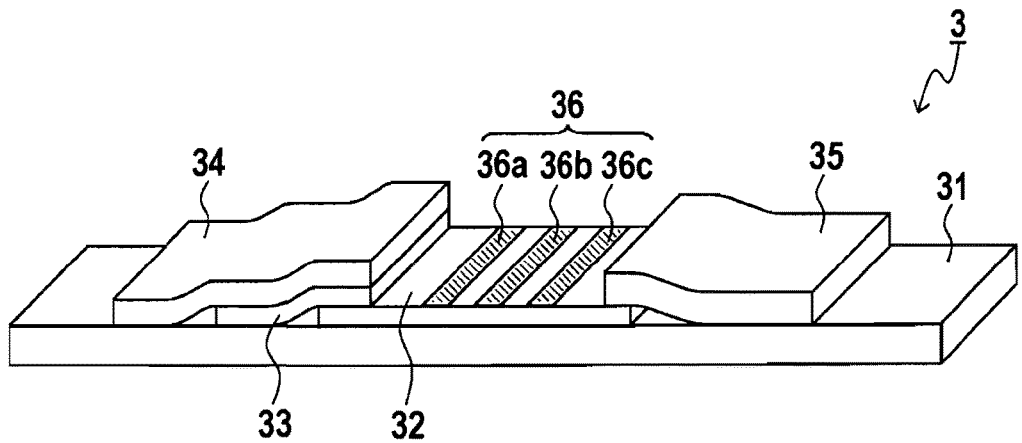
FIG. 2A is a perspective view showing an example of a test piece used in the present invention.
Figure 2B:
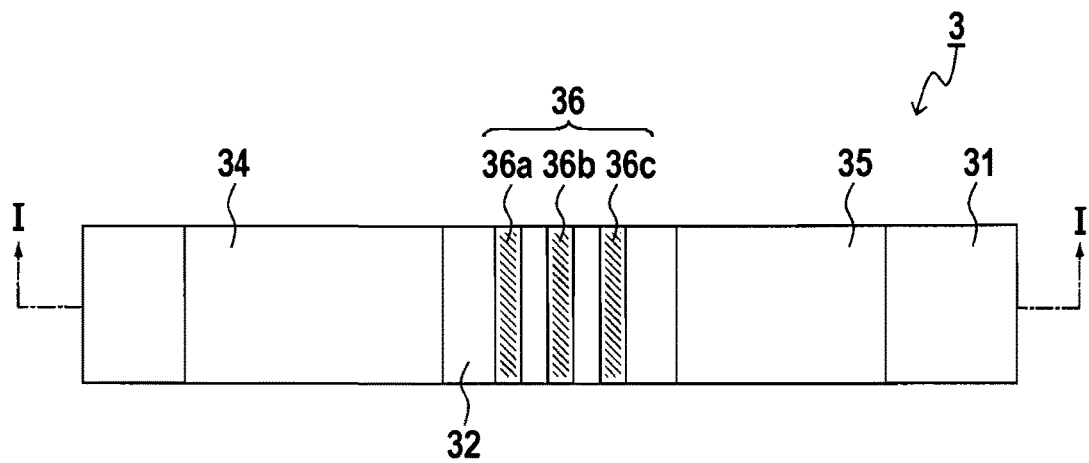
FIG. 2B is a plan view of the test piece shown in FIG. 2A.
Figure 2C:
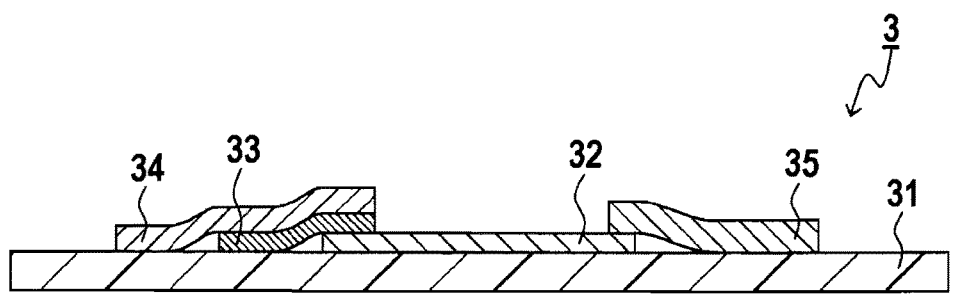
FIG. 2C is a sectional view of the test piece shown in FIG. 2B, viewed along arrows I-I in FIG. 2B.

Next, the test piece 3 used in the present example is shown in FIG. 2. FIG. 2A is a perspective view of the test piece 3, FIG. 2B is a plan view (top view) of the test piece 3 shown in FIG. 2A, and FIG. 2C is a sectional view of the test piece 3 shown in FIG. 2B, viewed along arrows I-I in FIG. 2B. In FIGS. 2A, 2B, and 2C, common components are given the same reference numerals. As shown in the drawings, the test piece 3 of the present example is of the lateral-flow type. In the test piece 3, a porous membrane 32 is disposed on a central portion of a support 31. On the porous membrane 32, the immobilized antibodies are immobilized so as to form lines, thereby providing measurement regions 36a, 36b, and 36c in the line forms. In the present example, the measurement region 36a is an influenza A virus detection region on which anti-influenza A virus monoclonal antibodies are immobilized; the measurement region 36b is an influenza B virus detection region on which anti-influenza B virus monoclonal antibodies are immobilized, and the measurement region 36c is a control detection region on which antimouse IgG polyclonal antibodies are immobilized. On one end side of the porous membrane 32 (the left in FIG. 2), a labeled antibody impregnated pad 33 is disposed so that a part thereof is laminated on the porous membrane 32, and a sample pad 34 is disposed on the labeled antibody impregnated pad 33. In the present example, the labeled antibody impregnated pad 33 is impregnated with blue latex-labeled anti-influenza A monoclonal antibodies and red latex-labeled anti-influenza B monoclonal antibodies. On the other end side of the porous membrane 32 (the right in FIG. 2), an absorption pad 35 is disposed so that a part thereof is laminated on the porous membrane 32. As described above, the test piece 3 is contained in the case body 21, the measurement regions 36a, 36b and 36c are located at the measurement window 23 and are exposed therefrom, and the sample pad 34 is located under the sample hole 22.

In the present invention, the porous membrane is not particularly limited, and preferably is one that exhibits a capillary action. Examples of the porous membrane include cellulose membranes, membranes formed of cellulose derivatives such as cellulose acetate and nitrocellulose, glass filters, and filter papers. In the present invention, the shape of the porous membrane is not particularly limited, and can be, for example, rectangular, circular, or the like. In the present invention, the size of the porous membrane is not particularly limited and can be set as appropriate.

The material of the support is not particularly limited, and it is possible to use the support formed of polyethylene terephthalate, polyethylene, polystyrene, polyester, cellulose acetate, or the like, for example. The shape of the support may be any of a film-like shape, a sheet-like shape, and a plate-like shape. The shape and the size of the support are not particularly limited, and can be set as appropriate depending on the configuration of the test piece.

The material of the labeled antibody impregnated pad is not particularly limited, and is, for example, polyethylene, glass fiber, rayon, nylon, paper, cellulose, or the like. In the present example, the labeled antibody impregnated pad 33 is produced by, for example, carrying out impregnation with a buffer containing the labeled antibodies and then drying. The buffer is not particularly limited, and examples thereof include the above-described buffers. In the present invention, the shape and the size of the labeled antibody impregnated pad are not particularly limited, and can be set as appropriate.

The material of the sample pad is not particularly limited, and the materials described above as examples of the material of the labeled antibody impregnated pad, and the like may be used, for example. The shape and the size of the sample pad are not particularly limited, and can be set as appropriate. The material of the absorption pad also is not particularly limited, and examples thereof include the materials that can be used for forming the sample pad. The shape and the size of the absorption pad are not particularly limited, and can be set as appropriate.

In the test piece of the present example, the measurement regions are provided in the form of three lines extending in the width direction of the porous membrane 32. However, the present invention is not limited thereto. The number of the measurement regions can be set freely within the range from 1 to 10, for example. Furthermore, the shape of the measurement regions may be rectangular, circular, or the like, in addition to the line form.

The material of the case body is not particularly limited, and examples thereof include polyethylene, polystyrene, polypropylene, and ABS resins.

Figure 3:
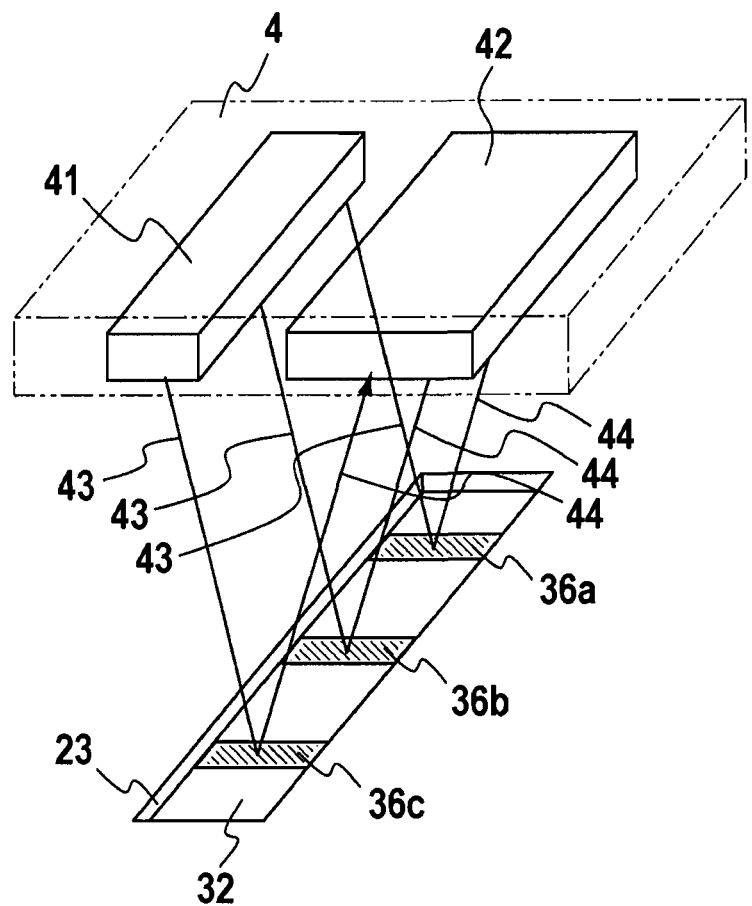
FIG. 3 is a schematic view showing an example of the relationship between a measurement unit and measurement regions in the immunoassay analyzer of the present invention.

Next, an example of an immunoassay method using the immunoassay analyzer of the present example will be described with reference to FIGS. 1 to 3. FIG. 3 shows the relationship between the measurement unit and the measurement regions shown in FIG. 1. It is to be noted, however, the immunoassay analyzer of the present invention is not limited thereto.

First, a specimen is collected by swabbing an inner wall of a pharyngeal region with a cotton swab. Then, a sample is prepared by immersing the cotton swab in the extractant to extract the specimen.

Figure 5A:
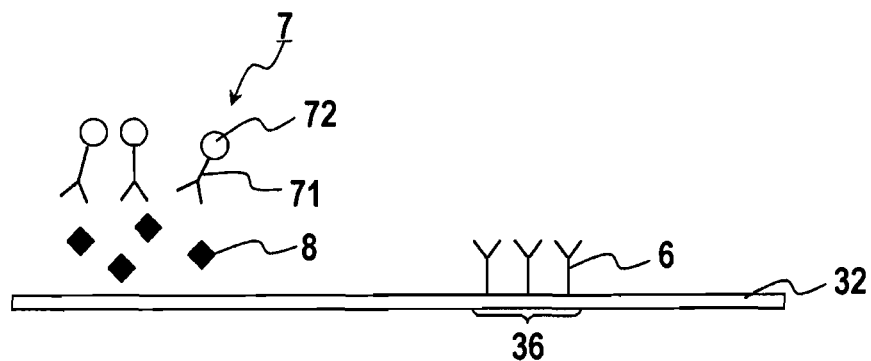
FIGS. 5A, 5B, and 5C are schematic views showing an example of the process of a color-developing reaction in an analysis method of the present invention.
Figure 5B:
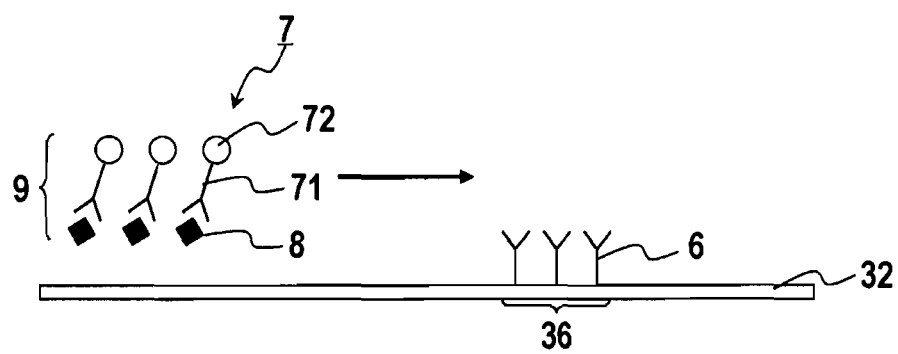
Figure 5C:
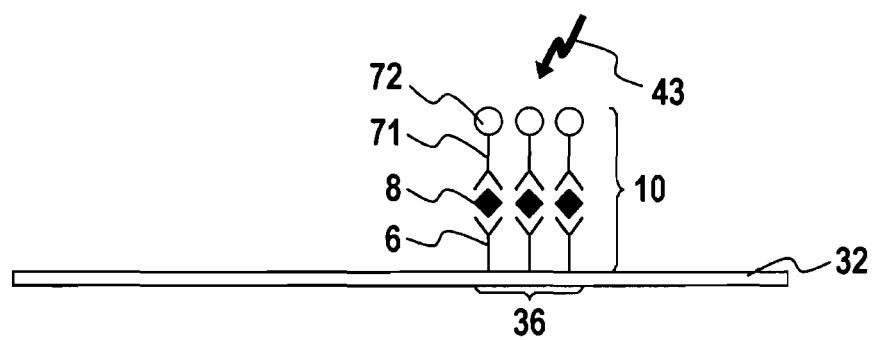

Next, the sample was dripped into the sample hole 22. Within 30 seconds after the dripping of the sample, the sample analysis tool 2 is inserted into the insertion slot 11. The dripping supplies the sample to the labeled antibody impregnated pad 33 via the sample pad 34 provided under the sample hole 22, and further, it dissolves the labeled antibodies impregnated in the labeled antibody impregnated pad 33. When the sample contains antigens as a substance to be detected, the labeled antibodies bind to the antigens through an antigen-antibody reaction, thereby forming labeled antibody-antigen conjugates. Then, the labeled antibody-antigen conjugates are developed in the porous membrane 32, and they bind to the immobilized antibodies in the measurement regions, thereby forming complexes. By the formation of the complexes, the measurement regions 36a to 36c are colored. A series of reactions described above will be described specifically with reference to schematic views of FIGS. 5A, 5B, and 5C. In each of FIGS. 5A to 5C, components identical to those in FIGS. 1 to 3 are given the same reference numerals. As shown in FIG. 5A, a porous membrane 32 having a measurement region 36 on which immobilized antibodies 6 are immobilized is provided. To an end on the side (the left side in FIG. 5A) opposite to the side where the measurement region 36 of the porous membrane 32 is located, a sample containing antigens 8, and labeled antibodies 7 are introduced. In FIG. 5A, reference numeral 71 denotes an antibody and reference numeral 72 denoted a label. As shown in FIG. 5B, the labeled antibodies 7 bind to the antigens 8, thereby forming labeled antibody-antigen conjugates 9. The conjugates 9 move in the longitudinal direction as indicated by an arrow owing to the capillary action of the porous membrane 32 and reach the measurement region 36. Then, as shown in FIG. 5C, the conjugates 9 bind to the immobilized antibodies 6 via the antigens 8, thereby forming complexes 10. As a result, the measurement region 36 is colored with the labels 72. The coloring is detected by irradiating the measurement region 36 with lights 43 having a main wavelength and a sub-wavelength, respectively. In the present example, the measurement region 36a is colored blue when influenza A antigens are contained in the sample, and the measurement region 36b is colored red when influenza B antigens are contained in the sample. Furthermore, the measurement region 36c is colored both blue and red when both the above-described labeled antibodies bind thereto. The measurement region 36c thus becomes purple, which indicates that both the labeled antibodies have been developed to (have reached) the measurement region. A residual part of the sample, not having been held in the measurement region 36, is absorbed by the absorption pad 35.

After a lapse of a predetermined time from the dripping of the sample, the coloring in the measurement region is measured by the measurement unit 4 in the following manner. The predetermined time is not particularly limited, and is, for example, in the range from 5 to 15 minutes. Then, in the measurement unit 4, the light source portion 41 emits the two kinds of irradiation lights 43 having wavelengths of 610 nm and 525 nm, respectively, so that the porous membrane 32 of the test piece 3, including the measurement regions 36a, 36b, and 36c, is irradiated with these lights, and the light receiving portion 42 measures reflected lights 44 of the respective wavelengths alternately at a time difference of 0.1 seconds or less. The measurement unit 4 moves above the sample analysis tool 2 in the X direction 45 (the short transverse direction of the sample analysis tool 2) while repeating the above-describe measurement, whereby it measures the reflected lights 44 from a region including all the measurement regions. In the present example, in the measurement line formed by the measurement region 36a, 610 nm serves as the main wavelength and 525 nm serves as the sub-wavelength. On the other hand, in the measurement line formed by the measurement region 36b, 525 nm serves as the main wavelength and 610 nm serves as the sub-wavelength.

Next, in the control and analysis portion 5, a reflectance is calculated from the measured value of each of the reflected lights. The reflectance may be calculated as, for example, the proportion of the measured value of the reflected light from the measurement line to the measured value of reflected light from a white piece as a control. Then, first, the reflectance at the main wavelength is compared with a standard value. When it is larger than the standard value, it is determined that the sample is "negative". When it is equal to or smaller than the standard value, the ratio (Rr=P/Q) between the reflectance (P) at the main wavelength and the reflectance (Q) at the sub-wavelength is determined. Then, the calculated value (Rr) of the ratio is compared with a previously determined standard value (Rrs) for the ratio. When the calculated value (Rr) of the ratio is equal to or smaller than the standard value (Rrs) for the ratio, it is regarded that the coloring is normal, so that it is determined that the sample is "positive". When the calculated value (Rr) of the ratio is larger than the standard value (Rrs) for the ratio, it is regarded that the coloring is abnormal, so that it is determined that "the determination is invalid". Then, the determination result is outputted from the output terminal. The obtained determination results may be stored in a memory. Furthermore, instead of the above-described determination method, it may be determined that the sample is "positive" when the calculated value (Rr) of the ratio is smaller than the standard value (Rrs) for the ratio and that "the determination is invalid" when the calculated value (Rr) of the ratio is equal to or larger than the standard value (Rrs) for the ratio. Note here that, although a reflectance is calculated from the measured value of the reflected light in the present example, a transmittance or an absorbance may be calculated and compared with a standard value therefor in the control and analysis portion 5, for example.

Figure 6A:
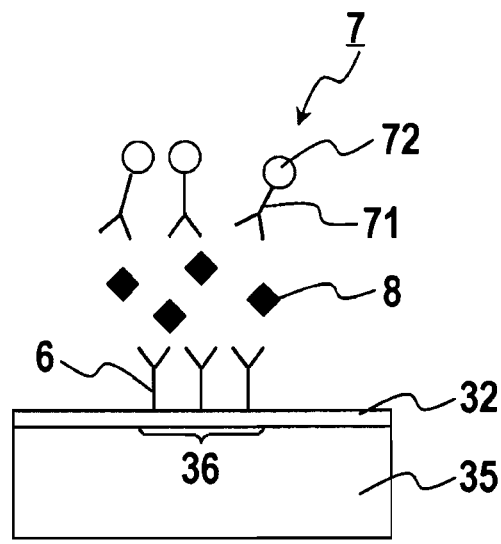
FIGS. 6A and 6B are schematic views showing an example of a detection step in a flow-through type test piece used in the present invention.
Figure 6B:
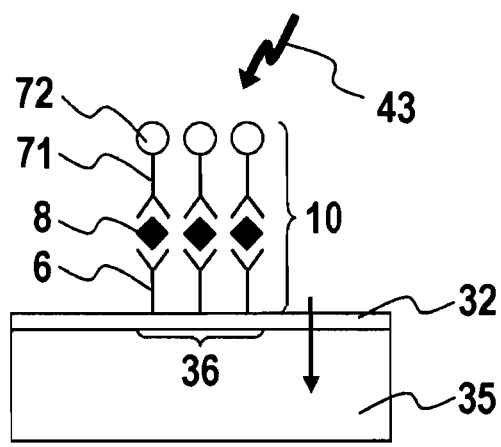

Although a lateral-flow type test piece is used in the present example, a flow-through type test piece may be used as described above. FIGS. 6A and 6B schematically show a series of processes of a detection step in a flow-through type test piece. In FIGS. 6A and 6B, components identical to those in FIGS. 1 to 5 are given the same reference numerals. As shown in FIG. 6A, a measurement region 36 is formed on a part of the upper surface of a porous membrane 32, and immobilized antibodies 6 are immobilized on the measurement region 36. Under the porous membrane 32, an absorption pad 35 is disposed so as to be in contact with the porous membrane 32. From above the measurement region 36 of the porous membrane 32, a sample containing antigens 8, and labeled antibodies 7 are introduced. As shown in FIG. 6B, the labeled antibodies 7 bind to the antigens 8, thereby forming labeled antibody-antigen conjugates 9, and the conjugates 9 bind to the immobilized antibodies 6 via the antigens 8, thereby forming complexes 10. As a result, the measurement region 36 is colored with labels 72. Furthermore, a liquid and the like other than these components in the sample pass through the porous membrane 32 in the thickness direction as indicated by an arrow and then are absorbed in the absorption pad 35. Then, the coloring is detected by irradiating the measurement region 36 with lights 43 having a main wavelength and a sub-wavelength by the light source portion 41. In the present example, the light receiving portion 42 measures reflected lights 44 resulting from the irradiation of the lights having the two wavelengths alternately at a time difference. It is to be noted that, although a reflectance is used as an optical signal in the present example, the present invention is not limited thereto. In the case where the optical signal is an absorbance or a transmittance, for example, transmitted light may be measured by disposing the measurement unit 4 under the sample analysis tool 2, and an absorbance or a transmittance may be calculated in the control and analysis portion 5. In this case, the sample analysis tool 2 preferably is configured so that the measurement window 23 serves as a light irradiation portion and another measurement window for detecting a transmittance, from which the measurement region 36 of the test piece is exposed, is formed on the opposite side of the measurement window 23.

<Immunoassay Method>

Next, the immunoassay method of the present invention is, as described above, an immunoassay method for determining the presence or absence of a substance to be detected in a sample by detecting color change due to a specific immunoreaction in a sample analysis tool. The immunoassay method includes an optical detection step of detecting the color change in the sample analysis tool, and a determination step of determining the presence or absence of the substance to be detected based on information obtained in the optical detection step. Unless otherwise stated, the method described in the explanation of the immunoassay analyzer of the present invention is applicable.

The optical detection step includes an optical signal measurement step of measuring an optical signal at each of two or more different wavelengths including a main wavelength for detecting color detection due to the specific immunoreaction and a sub-wavelength other than the main wavelength. The optical detection step may include a step(s) other than the optical signal measurement step, for example. The other step(s) is not particularly limited.

The determination step includes a discrimination step of comparing the respective optical signals at the two or more different wavelengths and discriminating between the color change due to the specific immunoreaction and color change due to a cause other than the specific immunoreaction based on a comparison criterion determined previously. The determination step may include a step(s) other than the discrimination step, for example. The other step(s) is not particularly limited.

In the immunoassay method of the present invention, the kind of the optical signal is not particularly limited, and the optical signal can be, for example, an absorbance, a reflectance, a transmittance, or the like.

The immunoassay method of the present invention may be configured so that, in the discrimination step, the comparison criterion is, for example, a standard value for a magnitude relationship between the optical signal at the main wavelength and the optical signal at the sub-wavelength, the optical signal at the main wavelength is compared with the optical signal at the sub-wavelength based on the standard value for the magnitude relationship, and the color change due to the specific immunoreaction and the color change due to a cause other than the specific immunoreaction are discriminated based on a result of the comparison. As described above, the number of sub-wavelengths may be one or may be two or more, for example. The immunoassay method of the present invention may be embodied, for example, in the form of analysis using two wavelengths as the former case, or in the form of analysis using three or more wavelengths as the latter case.

In immunoassay method of the present invention, examples of the comparison between the optical signal at the main wavelength and the optical signal at the sub-wavelength include, as described above, comparison using a ratio and comparison using a difference.

It is preferable that, in the determination step, for example, it is determined that the sample is negative when the optical signal at the main wavelength indicates that no color change of the sample analysis tool is detected based on a previously determined standard, and whether the detected color change is due to the specific immunoreaction or a cause other than the specific immunoreaction is discriminated in the discrimination step.

It is preferable that, in the determination step, for example, when the absorbance at the main wavelength is smaller than the previously determined standard value (or equal to or smaller than the standard value), it is determined that the sample is negative, and when the absorbance at the main wavelength is equal to or larger than the standard value (or larger than the standard value), whether the detected color change is due to the specific immunoreaction or a cause other than the specific immunoreaction is discriminated in the discrimination step. There is no particularly limitation on the setting of the standard value, and the standard value may be set, for example, based on data collected beforehand as described above.

In the discrimination step, whether the color change due to a cause other than the specific immunoreaction is due to a nonspecific reaction or a cause other than immunoreactions further may be discriminated. The color change due to a nonspecific reaction and the color change due to a cause other than immunoreaction are, for example, as described above. The method for discriminating whether the color change due to a cause other than the specific immunoreaction is either of the above-described two kinds of color changes is, for example, as described above.

EXAMPLES

Next, examples of the immunoassay analyzer according to the present invention will be described together with comparative examples. It should be noted, however, the present invention is by no means limited or restricted by the following examples and comparative examples.

Example 1

Figure 4A:
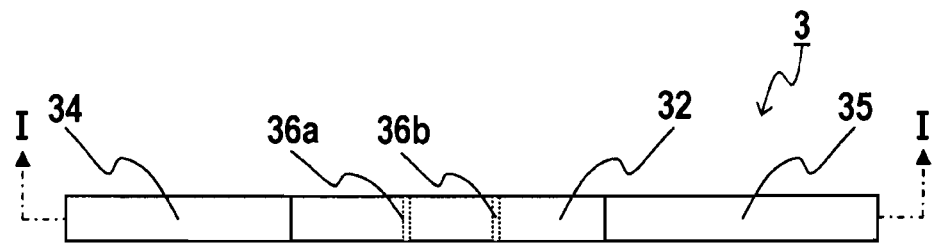
FIG. 4A a plan view showing another example of the test piece used in the present invention.
Figure 4B:
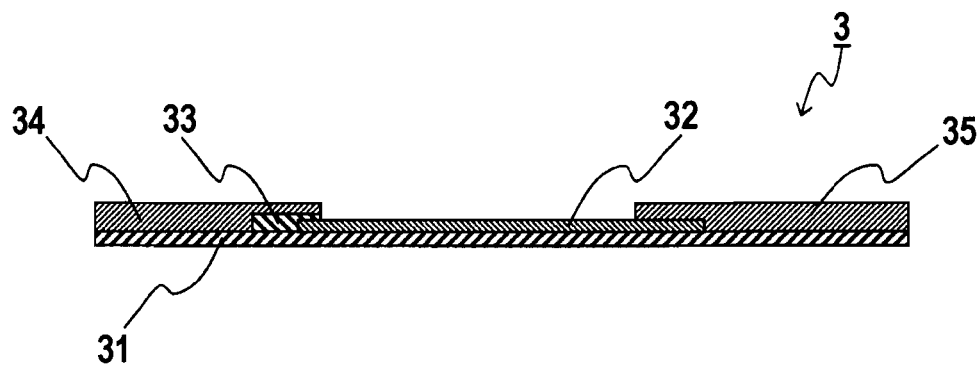
FIG. 4B is a sectional view of the test piece shown in FIG. 4A, viewed along arrows I-I in FIG. 4A.
Figure 4C:
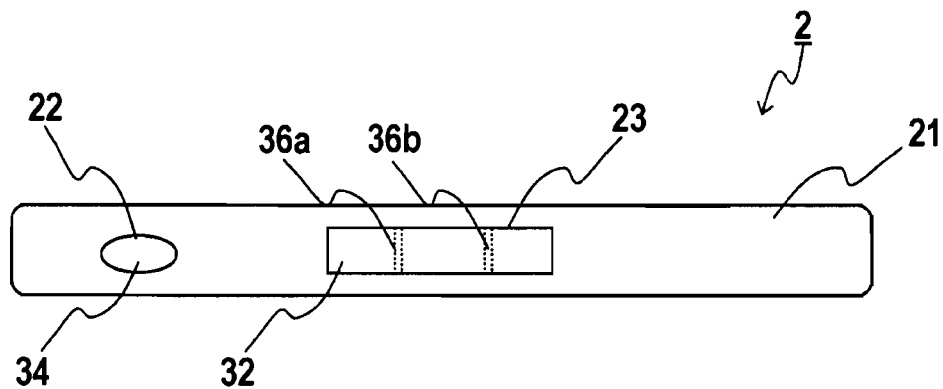
FIG. 4C is a plan view showing a sample analysis tool containing the test piece shown in FIGS. 4A and 4B.

In the present example, influenza A and B viruses in a sample were detected using the immunoassay analyzer shown in FIG. 1. In the present example, a sample analysis tool shown in FIG. 4 was used. FIG. 4A is a plan view (top view) of a test piece 3, FIG. 4B is a sectional view of the test piece 3, viewed along arrows I-I in FIG. 4A, and FIG. 4C is a plan view (top view) showing the sample analysis tool 2 in which the test piece 3 shown in FIGS. 4A and 4B is contained in a case body 21. In FIG. 4, components identical to those in FIGS. 1 to 3 are given the same reference numerals. This sample analysis tool 2 has the same configuration as those of the sample analysis tools shown in FIGS. 1 to 3, except that the control detection region 36c is not formed therein.

<Production of Sample Analysis Tool for Influenza Virus Detection>

The sample analysis tool used in the present example was produced in the following manner.

(1) Preparation of Blue Latex-Labeled Anti-Influenza A Virus Monoclonal Antibody Solution First, blue latex particles (particle diameter: 0.3 μm, Ceradyne, Inc.) were suspended in a 20 mmol/l boric acid buffer (pH 8.2). Anti-influenza A virus monoclonal antibodies (Fitzgerald Industries International) further were added thereto, and the mixture was allowed to react at room temperature for 60 minutes. The reaction solution was centrifuged, and the supernatant was removed. Thereafter, a 1 w/v % bovine serum albumin-containing boric acid buffer (pH 8.2) was added thereto to resuspend the particles. The suspension obtained by this resuspension was centrifuged, and thereafter, the supernatant was removed. The collected antibodies were suspended in a latex dispersion buffer having the following composition. Thus, a blue latex-labeled anti-influenza A virus monoclonal antibody solution was prepared.

(Composition of Latex Dispersion Buffer)

| Component | Concentration |
| --- | --- |
| Tris buffer (pH 8.4) | 25 mmol/l |
| NaCl | 100 mmol/l |
| Bovine serum albumin (BSA) | 1 w/v % |

(2) Preparation of Red Latex-Labeled Anti-Influenza B Virus Monoclonal Antibody Solution A red latex-labeled anti-influenza B virus monoclonal antibody solution was prepared in the same manner as that for the blue latex-labeled anti-influenza A virus monoclonal antibody solution, except that red latex particles (particle diameter: 0.3 μm, Ceradyne, Inc.) were used instead of the blue latex particles and that anti-influenza B virus monoclonal antibodies (Fitzgerald Industries International) were used instead of the anti-influenza A virus monoclonal antibodies.

(3) Production of Components

First, components of the test piece were provided in the following manner.

Production of Labeled Antibody Impregnated Pad

The blue latex-labeled anti-influenza A virus monoclonal antibody solution and the red latex-labeled anti-influenza B virus monoclonal antibody solution were mixed at a ratio of 1:1 (volume ratio). A glass filter (Millipore Corporation) cut so as to have a width of 1 cm and a length of 30 cm was impregnated with the mixture and dried using a dryer at 70° C. for 45 minutes. Thus, a labeled antibody impregnated pad 33 was produced.

Production of Antibody Immobilized Membrane

A nitrocellulose membrane (Millipore Corporation) was cut into a strip shape having a width of 3 cm and a length of 30 cm. This membrane was set in an antibody applicator (BioDot, Inc), and anti-influenza A virus monoclonal antibodies (Fitzgerald Industries International) were applied on a line at a distance of 11 mm from one longitudinal side edge of the strip, thus providing a measurement region 36a. Furthermore, anti-influenza B virus monoclonal antibodies (Fitzgerald Industries International) were applied on a line at a distance of 15 mm from the longitudinal side edge of the strip, thus providing a measurement region 36b. The membrane to which the antibodies were applied was dried using a dryer at 40° C. for 20 minutes. Thus, an antibody immobilized membrane 32 was produced.

Production of Sample Pad, Absorption Pad, and Support

A sample pad 34 was produced by cutting a filter paper (Millipore Corporation) so as to have a width of 2.6 cm and a length of 30 cm. An absorption pad 35 was produced by cutting a filter paper (Whatman plc.) so as to have a width of 2.9 cm and a length of 30 cm. A support 31 was produced by cutting a plastic sheet provided with a two-sided tape so as to have a width of 7.7 cm and a length of 30 cm.

(4) Production of Test Piece

The test piece 3 was produced in the following manner. In FIG. 4, the left side is an upstream side and the right side is a downstream side. First, the antibody immobilized membrane 32 was attached to a central portion of the support 31 with the measurement region 36a being on the upstream side (the left side in FIG. 4). The absorption pad 35 was attached so as to extend from an end portion of the antibody immobilized membrane 32 on the measurement region 36b side to an end portion of the support 31 on the downstream side (the right side in FIG. 4). Then, the labeled antibody impregnated pad 33 was attached so as to extend from an end portion of the antibody immobilized membrane 32 on the measurement region 36a side to an end portion of the support 31 on the upstream side with the labeled antibody impregnated pad 33 and the antibody immobilized membrane 32 overlapping one another in the longitudinal direction by 1 mm. On the labeled antibody impregnated pad 33, the sample pad 34 was laminated. After the respective components were laminated as described above, the laminate was cut into a strip having a width of 4 mm. Thus, the test piece 3 having a width of 4 mm and a length of 77 mm was produced.

(5) Production of Sample Analysis Tool

The test piece 3 was contained in the case body 21 having a sample hole 22 and a measurement window 23. Thus, the sample analysis tool 2 used in the present example was produced.

<Detection of Influenza Viruses>

Using the sample analysis tool 2, influenza viruses in specimens were analyzed in the following manner. As the specimens, nasal aspirates collected with a tracheal catheter having a trap attached thereto were used. In the present example, the presence or absence of influenza viruses in the specimens was checked by a RT-PCR method shown in the following item (6). Then, with respect to the specimens having undergone the checking, the presence or absence of the viruses was determined by the immunoassay analyzer of the present example and visual observation.

(6) Detection of Influenza Viruses According to RT-PCR Method

In the present example, the RT-PCR method was carried out using a method for detecting matrix proteins of influenza A and B viruses, proposed by Wangdong Zhang and David. H. Evans (Journal of Virological methods, 1991, vol. 33, pp. 165-189).

(7) Detection of Influenza Viruses by Immunoassay Analyzer

With respect to four negative specimens in which influenza viruses had not been detected by the RT-PCR method, three A-positive specimens in which influenza A viruses had been detected by the RT-PCR method, and B-positive specimens in which influenza B viruses had been detected by the RT-PCR method, measurement was performed using the sample analysis tool 2 in the following manner. First, each of the nasal aspirates was suspended in a specimen extractant having the following composition, and 120 μl of the thus-obtained suspension was dripped into the sample hole 22. 15 minutes after the dripping, a region including the measurement regions 36a and 36b was irradiated with lights having two different wavelengths (610 nm, 525 nm) with the use of the immunoassay analyzer 1 of the present example, and the reflectances in the measurement regions were measured. For the detection of the influenza A viruses, 610 nm was used as the main wavelength, and 525 nm was used as the sub-wavelength. On the other hand, for the detection of the influenza B viruses, 525 nm was used as the main wavelength, and the 610 nm was used as the sub-wavelength.

(Composition of Specimen Extractant)

| Component | Concentration |
| --- | --- |
| Tris buffer (pH 7.5) | 50 mmol/l |
| Tween 20 | 0.5 w/v % |
| NaCl | 0.9 w/v % |
| BSA | 1 w/v % |

Next, using the thus-obtained respective reflectances, the presence or absence of the influenza viruses was determined in the same manner as described above. In the present example, a standard value for the reflectance at the main wavelength used for negative determination was set to 99%. Furthermore, the ratio to be calculated was set to "Rr=P/Q" as described above, and the standard value (Rrs) for the ratio was set to 0.99.

(8) Detection of Influenza Viruses by Visual Observation

Also, whether or not the measurement regions 36a and 36b were colored was checked by visual observation to determine the presence or absence of the influenza viruses. In the determination by the visual observation, it was determined that: the sample was influenza A positive when the measurement region 36a was blue; the sample was influenza B positive when the measurement region 36b was red; the sample was negative for either type of influenza when neither of the measurement regions was colored; and the determination was invalid when the color of each of the measurement regions was other than blue and red and in the case of the adhesion of dust or a flaw on the membrane.

Comparative Example 1

In the present example, measurement was performed in the same manner as in Example 1, except that irradiation was performed using, instead of the lights having two different wavelengths, only light having a wavelength of 610 nm for influenza A virus detection and only light having a wavelength of 525 nm for influenza B virus detection. Furthermore, in the present example, it was determined that the sample was negative when the reflectance at the main wavelength was larger than 99% and that the sample was positive when the reflectance at the main wavelength was equal to or smaller than 99%.

Table 1 below shows analysis results obtained in Example 1 and Comparative Example 1. In Table 1, "−" indicates negative and "+" indicates positive. As can be seen from Table 1, in Comparative Example 1, the determination results for three specimens (specimens No. 3, No. 4, and No. 10) out of the ten specimens did not agree with those obtained by the visual observation. In contrast, in Example 1, the determination results for all the specimens agreed with those obtained by the visual observation. The specimen No. 3 was negative for both the influenza A and influenza B according to the determination by the RT-PCR method. However, in the determination by the visual observation, purple coloring due to a nonspecific reaction derived from the specimen was observed in the measurement region 36a for influenza A virus detection. As to the coloring due to the nonspecific reaction, the analysis method of Comparative Example 1 made an incorrect determination that the specimen was influenza A positive. In contrast, according to the analysis method of Example 1, the result of analysis as to the influenza A was determined as invalid, which means that the analysis method of Example 1 could make a correct determination as to the coloring due to the nonspecific reaction. Furthermore, the specimen No. 4 was negative for both the influenza A and influenza B according to the determination by the RT-PCR method. However, owing to dirt adhered to the measurement region 36b for influenza B virus detection, it was determined that the determination was invalid in the determination as to the influenza B by the visual observation. As to the dirt in the measurement region, the analysis method of Comparative Example 1 made an incorrect determination that the specimen was influenza B positive. In contrast, according to the analysis method of Example 1, the result of analysis as to influenza B was determined as invalid, which means the analysis method of Example 1 could make a correct determination as to the dirt in the measurement region. Still further, the specimen No. 10 was influenza A negative and influenza B positive according to the determination by the RT-PCR method. However, in the determination by the visual observation, purple coloring due to a nonspecific reaction derived from the specimen was observed in the measurement region 36a for influenza A virus detection. As to the coloring due to the nonspecific reaction, the analysis method of Comparative Example 1 made an incorrect determination that the specimen was influenza A positive. In contrast, according to the analysis method of Example 1, the result of analysis as to influenza A was determined as invalid, which means the analysis method of Example 1 could make a correct determination as to the dirt in the measurement region. Moreover, as to the red coloring observed in the measurement region 36b for influenza B virus detection, the determination was made correctly in both Comparative Example 1 and Example 1.

TABLE 1

| Specimen No. | Type of virus | Reflectance Main wavelength | Reflectance Sub-wavelength | Ratio | Determination Ex. 1 | Determination Comp. Ex. 1 | RT-PCR method | Visual observation Determination | Visual observation Presence or absence of line |
|---|---|---|---|---|---|---|---|---|---|
| 1 | A | 100% | 100% |  | − | − | − | − | no line |
|  | B | 100% | 100% |  | − | − | − | − | no line |
| 2 | A | 100% | 100% |  | − | − | − | − | no line |
|  | B | 100% | 100% |  | − | − | − | − | no line |
| 3 | A | 97% | 97% | 1.00 | invalid | + | − | invalid | purple |
|  | B | 100% | 101% |  | − | − | − | − | no line |
| 4 | A | 100% | 101% |  | − | − | − | − | no line |
|  | B | 93% | 91% | 1.02 | invalid | + | − | invalid | dirt |
| 5 | A | 79% | 92% | 0.86 | + | + | + | + | blue |
|  | B | 100% | 100% |  | − | − | − | − | no line |
| 6 | A | 48% | 69% | 0.70 | + | + | + | + | blue |
|  | B | 100% | 100% |  | − | − | − | − | no line |
| 7 | A | 96% | 98% | 0.98 | + | + | + | + | blue |
|  | B | 100% | 100% |  | − | − | − | − | no line |
| 8 | A | 100% | 100% |  | − | − | − | − | no line |
|  | B | 91% | 99% | 0.92 | + | + | + | + | red |
| 9 | A | 100% | 100% |  | − | − | − | − | no line |
|  | B | 84% | 98% | 0.86 | + | + | + | + | red |
| 10 | A | 99% | 98% | 1.01 | invalid | + | − | invalid | purple |
|  | B | 71% | 93% | 0.76 | + | + | + | + | red |

Example 2

In the present example, group A hemolytic streptococci (hereinafter referred to as group A streptococci) in specimens were detected in the same manner as in Example 1, using the immunoassay analyzer shown in FIG. 1. A test piece used in the present example has the same configuration as the test piece used in Example 1, except that the labeled antibody impregnated pad 33 contained anti-group A *streptococcus* antibodies instead of the anti-influenza A virus monoclonal antibodies and anti-influenza B virus monoclonal antibodies, the test piece had one measurement region 36a in a line form, and the sizes of the respective pads and membranes were different from those in the test piece of Example 1 as will be described later.

<Production of Test Piece for Group A *Streptococcus* Detection>

The test piece 3 used in the present example was produced in the following manner.

(1) Production of Blue Latex-Labeled Anti-Group A *Streptococcus* Polyclonal Antibody Solution In the present example, a blue latex-labeled anti-group A *streptococcus* polyclonal antibody solution was prepared in the same manner as in Example 1, except that the anti-group A *streptococcus* polyclonal antibodies (goat, Fitzgerald Industries International) were used instead of the anti-influenza A virus monoclonal antibodies.

(2) Production of Test Piece

Components of the test piece were provided in the following manner. The test piece of the present example was produced in the same manner as in Example 1, except that these components were used instead of the respective components in Example 1.

Production of Labeled Antibody Impregnated Pad

In the present example, a labeled antibody impregnated pad 33 was produced in the same manner as in Example 1, except that the length of the glass filter was set to 25 cm instead of 30 cm and the blue latex-labeled anti-group A *streptococcus* polyclonal antibody solution was used instead of the above-described mixture.

Production of Antibody Immobilized Membrane

In the present example, an antibody immobilized membrane 32 was produced in the same manner as in Example 1, except that the length of the nitrocellulose membrane was set to 25 cm instead of 30 cm, anti-group A *streptococcus* polyclonal antibodies (rabbit, Fitzgerald Industries International) were used instead of the anti-influenza A virus monoclonal antibodies, and no antibodies were applied onto the measurement region 36b that was on a line at a distance of 15 mm from the edge of the nitrocellulose membrane.

Production of Sample Pad, Absorption Pad, and Support

In the present example, a sample pad 34, an absorption pad 35, and a support 31 were produced in the same manner as in Example 1, except that the length of each of the glass filter, the filter paper, and the plastic sheet was set to 25 cm instead of 30 cm.

<Detection of Group A Streptococci>

Using the sample analysis tool 2, group A streptococci in specimens were analyzed in the following manner. As the specimens, throat swabs collected with a cotton swab were used. In the present example, the presence or absence of group A streptococci in the specimens was checked using a culture method shown in the following item (3), and with respect to the specimens having undergone the checking, the presence or absence of the group A streptococci was determined by the immunoassay analyzer of the present example and visual observation.

(3) Detection of Group A Streptococci by Culture Method

In the present example, the specimens were cultured in the following manner. First, each of the specimens was suspended in physiological saline. The suspension was smeared on a sheep blood agar medium and cultured in a carbon dioxide incubator at 36° C. for 1 to 2 days. After the completion of the culture, colonies showing β hemolysis were collected and cultured in the same manner as described above. The thus-obtained colonies were divided into groups using a latex agglutination assay kit (Mitsubishi Chemical Medience Corporation), and the presence or absence of the group A streptococci in the specimens was checked.

(4) Detection of Group A Streptococci by Immunoassay Analyzer

With respect to four negative specimens in which the group A streptococci had not been detected by the culture method and four positive specimens in which the group A streptococci had been detected by the culture method, measurement was performed using the sample analysis tool 2 in the following manner. First, an extraction treatment was performed by suspending each of the throat swabs in a mixture of 0.4 ml of an extractant A (0.2 mol/l citric acid aqueous solution) and 0.2 ml of an extractant B (2 mol/l sodium nitrite aqueous solution) and then allowing the resultant mixture to stand for 1 minute. The solution having undergone the extraction treatment was neutralized using 0.1 ml of an extractant C (1 mol/l tris(hydroxymethyl) aminomethane). The resultant treated specimen solution was used as a sample. 90 µl of this sample was dripped into the sample hole 22. 10 minutes after the dripping, a region including the measurement region 36a was irradiated with lights having two different wavelengths (610 nm, 525 nm) with the use of an immunoassay analyzer 1 of the present example, and the reflectances in the measurement region 36a were measured. For the detection of the group A streptococci, 610 nm was used as the main wavelength and 525 nm was used as the sub-wavelength.

Next, using the thus-obtained respective reflectances, the presence or absence of the group A streptococci was determined. In the present example, the determination was carried out using the same standard value and the same determination method as in Example 1.

(5) Detection of Group A Streptococci by Visual Observation

Also, whether or not the measurement region 36a was colored was checked by visual observation, and the presence or absence of the group A streptococci was determined. In the determination by the visual observation, it was determined that: the sample was positive for the group A streptococci when the measurement region 36a was blue; the sample was negative for the group A streptococci when the measurement region 36a was not colored; and the determination was invalid when the color of the measurement region 36a was other than blue and in the case of the adhesion of dust or a flaw on the membrane.

Comparative Example 2

In the present example, measurement was performed in the same manner as in Example 2, except that irradiation was performed using, instead of the lights having two different wavelengths, only light having a wavelength of 610 nm. Furthermore, in the present example, it was determined that the sample was negative when the reflectance at the main wavelength was larger than 99% and that the sample was positive when the reflectance at the main wavelength was equal to or smaller than 99%.

Table 2 below shows analysis results obtained in Example 2 and Comparative Example 2. In Table 2, "−" indicates negative and "+" indicates positive. As can be seen from Table 2, in Comparative Example 1, the determination results for two specimens (specimens No. 3 and No. 4) out of the eight specimens did not agree with those obtained by the visual observation. In contrast, in Example 1, the determination results for all the specimens agreed with those obtained by the visual observation. The specimen No. 3 was negative according to the culture method. However, in the determination by the visual observation, although no coloring was observed, it was determined that the determination was invalid owing to a flaw on the membrane in the measurement region 36a. As to the flaw in the measurement region, the analysis method of Comparative Example 2 made an incorrect determination that the specimen was positive. In contrast, according to the analysis method of Example 2, it was determined that the determination was invalid, which means the analysis method of Example 2 could make a correct determination as to the flaw. Furthermore, the specimen No. 4 was negative according to the culture method. However, owing to dust (hair) adhered to the measurement region 36a, it was determined that the determination was invalid in the determination by the visual observation. As to the dust in the measurement region, the analysis method of Comparative Example 2 made an incorrect determination that the specimen was positive. In contrast, according to the analysis method of Example 2, it was determined that the determination was invalid, which means the analysis method of Example 2 could make a correct determination as to the dust in the measurement region.

TABLE 2

| | Reflectance | | | Determination | | | Visual observation | |
| --- | --- | --- | --- | --- | --- | --- | --- | --- |
| Specimen No. | Main wavelength | Sub-wavelength | Ratio | Ex. 2 | Comp. Ex. 2 | Culture method | Determination | Presence or absence of line |
| 1 | 100% | 100% | | − | − | − | no line | − |
| 2 | 100% | 100% | | − | − | − | no line | − |
| 3 | 99% | 99% | 1.00 | invalid | + | − | no line (flaw) | invalid |
| 4 | 92% | 90% | 1.02 | invalid | + | − | no line (dust) | invalid |
| 5 | 86% | 95% | 0.91 | + | + | + | blue | + |
| 6 | 95% | 99% | 0.96 | + | + | + | blue | + |
| 7 | 74% | 89% | 0.83 | + | + | + | blue | + |
| 8 | 97% | 99% | 0.98 | + | + | + | blue | + |

Example 3

In the present example, RS viruses in specimens were detected using the immunoassay analyzer 1 shown in FIG. 1. A test piece used in the present example has the same configuration as the test piece used in Example 2, except that gold colloid particles were contained instead of the blue latex particles, and the labeled antibody impregnated pad 33 contained anti-RS virus antibodies instead of the anti-group A *streptococcus* antibodies.

<Production of Test Piece for RS Virus Detection>

The test piece used in the present example was produced in the following manner.

(1) Production of Gold Colloid-Labeled Anti-RS Virus Monoclonal Antibody Solution In the present example, a gold colloid-labeled anti-RS virus monoclonal antibody solution was prepared in the same manner as in Example 2, except that gold colloid particles (particle diameter: 20 nm, BBI) were used instead of the blue latex particles, anti-RS virus monoclonal antibodies (Fitzgerald Industries International) were used instead of the anti-group A *streptococcus* polyclonal antibodies, and a gold colloid dispersion buffer (20 mmol/l Tris buffer, pH 8.0) was used instead of the latex dispersion buffer.

(2) Production of Test Piece

The test piece of the present example was produced in the same manner as in Example 2, except that components described below were used as a labeled antibody impregnated pad, an antibody immobilized membrane, and a sample pad, respectively, instead of those in Example 2.

Production of Labeled Antibody Impregnated Pad

In the present example, a labeled antibody impregnated pad 33 was produced in the same manner as in Example 2, except that the gold colloid-labeled anti-RS virus monoclonal antibody solution was used instead of the blue latex-labeled anti-group A *streptococcus* polyclonal antibody solution.

Production of Antibody Immobilized Membrane

In the present example, an antibody immobilized membrane 32 was produced in the same manner as in Example 2, except that anti-RS virus monoclonal antibodies (Fitzgerald Industries International) were used instead of the anti-group A *streptococcus* polyclonal antibodies.

Production of Sample Pad

In the present example, a sample pad 34 was produced in the same manner as in Example 2, except that a filter paper (Millipore Corporation) was used instead of the glass filter.

<Detection of RS Viruses>

Using the sample analysis tool 2, RS viruses in specimens were analyzed in the following manner. As the specimens, the above-described nasal aspirates were used. In the present example, the presence or absence of the RS viruses in the specimens was checked using a RT-PCR method shown in the following item (3), and with respect to the specimens having undergone the checking, the presence or absence of the RS viruses was determined by the immunoassay analyzer of the present example and visual observation.

(3) Detection of RS Viruses by RT-PCR Method

In the present example, the RT-PCR method was carried out using a method for detecting RS viruses proposed by J. Stockton et al. (Journal of Clinical Microbiology, 1998, vol. 36, No. 10, pp. 2990-2995).

(4) Detection of RS Viruses by Immunoassay Analyzer

With respect to four negative specimens in which RS viruses had not been detected by the RT-PCR method and four positive specimens in which RS viruses had been detected by the RT-PCR method, measurement was performed in the same manner as in Example 2, except that the test piece for RS virus detection was used instead of the test piece for influenza virus detection. For the detection of the RS viruses, 525 nm was used as the main wavelength and 610 nm was used as the sub-wavelength.

Next, using the thus-obtained respective reflectances, the presence or absence of the RS viruses was determined. In the present example, the determination was carried out using the same standard value and the same determination method as in Example 2.

(5) Detection of RS Viruses by Visual Observation

Also, whether or not the measurement region 36a was colored was checked by visual observation, and the presence or absence of the RS viruses was determined. In the determination by the visual observation, it was determined that: the sample was positive for the RS viruses when the measurement region 36a was red; the sample was negative for the RS viruses when the measurement region 36a was not colored; and the determination was invalid when the color of the measurement region 36a was other than red and in the case of the adhesion of dust or a flaw on the membrane.

Comparative Example 3

In the present example, measurement was performed in the same manner as in Example 3, except that irradiation was performed using, instead of the lights having two different wavelengths, only light having a wavelength of 525 nm. Furthermore, in the present example, the presence or absence of the RS viruses in the specimens was determined using the same standard value and the determination method as in Comparative Example 2.

Table 3 below shows analysis results obtained in Example 3 and Comparative Example 3. In Table 3, "−" indicates negative and "+" indicates positive. As can be seen from Table 3, in Comparative Example 3, the determination results for two specimens (specimens No. 3 and No. 4) out of the eight specimens did not agree with those obtained by the visual observation. In contrast, in Example 3, the determination results for all the specimens agreed with those obtained by the visual observation. The specimen No. 3 was negative according to the RT-PCR method. However, in the determination by the visual observation, although no coloring was observed, it was determined that the determination was invalid owing to a flaw on the membrane in the measurement region 36a. As to the flaw in the measurement region, the analysis method of Comparative Example 3 made an incorrect determination that the specimen was positive. In contrast, according to the analysis method of Example 3, it was determined that the determination was invalid, which means the analysis method of Example 3 could make a correct determination as to the flaw. Furthermore, the specimen No. 4 was negative according to the RT-PCR method. However, owing to dust (lint) adhered to the measurement region 36a, it was determined that the determination was invalid in the determination by the visual observation. As to the dust in the measurement region, the analysis method of Comparative Example 3 made an incorrect determination that the specimen was positive. In contrast, according to the analysis method of Example 3, it was determined that the determination was invalid, which means the analysis method of Example 3 could make a correct determination as to the dust in the measurement region.

TABLE 3

| Specimen No. | Reflectance Main wavelength | Reflectance Sub-wavelength | Ratio | Determination Ex. 3 | Determination Comp. Ex. 3 | RT-PCR method | Visual observation Determination | Visual observation Presence or absence of line |
|---|---|---|---|---|---|---|---|---|
| 1 | 100% | 100% | – | – | – | – | no line | – |
| 2 | 100% | 100% | – | – | – | – | no line | – |
| 3 | 95% | 94% | 1.01 | invalid | + | – | no line (flaw) | invalid |
| 4 | 96% | 96% | 1.00 | invalid | + | – | no line (dust) | invalid |
| 5 | 94% | 98% | 0.96 | + | + | + | red | + |
| 6 | 63% | 79% | 0.80 | + | + | + | red | + |
| 7 | 82% | 91% | 0.90 | + | + | + | red | + |
| 8 | 70% | 85% | 0.82 | + | + | + | red | + |

INDUSTRIAL APPLICABILITY

According to the present invention, it is possible to obtain a determination result while discriminating between normal coloring caused by a specific immunoreaction and abnormal coloring caused by a nonspecific reaction, dust or a flaw on a measurement region, or the like. The present invention is applicable to fields such as clinical tests, biochemical tests, and medical researches. The use of the present invention is not limited, and the present invention can be applied to a wide range of fields.

EXPLANATION OF REFERENCE NUMERALS 1 immunoassay analyzer
11 insertion slot
2 sample analysis tool
21 case body
22 sample hole
23 measurement window
3 test piece
31 support
32 porous membrane, antibody immobilized membrane
33 labeled antibody impregnated pad
34 sample pad
35 absorption pad
36, 36a, 36b, 36c measurement region
4 measurement unit, optical detection unit
41 light source portion
42 light receiving portion
43 irradiation light
44 reflected light
45 X direction
5 control and analysis portion, determination unit
6 immobilized antibody
7 labeled antibody
71 antibody
72 label
8 antigen
9 labeled antibody-antigen conjugate
10 complex

The invention claimed is:

1. An immunoassay analyzer comprising:
a light source portion for irradiating, with a main wavelength and a sub-wavelength other than the main wavelength, a measurement region of a test piece of a sample analysis tool containing a sample comprising a target substance in the measurement region where a color change is a result of a specific immunoreaction of the target substance;
an optical signal measurement unit for measuring optical signals of the measurement region at the main wavelength and the sub-wavelength;
a determination unit for determining, based on the optical signal measured at the main wavelength, that:
the sample is negative regarding the presence of the target substance when the optical signal measured at the main wavelength indicates no color change; or
the sample is either positive or invalid regarding the presence of the target substance when the optical signal measured at the main wavelength indicates the color change; and
a discrimination unit for comparing the respective optical signals at the main wavelength and the sub-wavelength to discriminate between the color change due to the specific immunoreaction and the color change due to a cause other than the specific immunoreaction based on a comparison criterion determined previously, wherein the comparison criterion is a standard value for a magnitude relationship between the optical signal at the main wavelength and the optical signal at the sub-wavelength, the discrimination unit determining, based on the optical signals of the measurement region at the main wavelength and the sub-wavelength, that:
the sample is positive regarding the presence of the target substance when the color change is due to the specific immunoreaction; or
the sample is invalid regarding the presence of the target substance when the color change is due to a cause other than the specific immunoreaction; and
an output terminal that displays a negative reading when the determination unit determines that the sample is negative; a positive reading when the discrimination unit determines that the sample is positive; and an invalid reading when the discrimination unit determines that the sample is invalid.

2. The immunoassay analyzer according to claim 1, wherein the optical signal is at least one selected from the group consisting of an absorbance, a reflectance, and a transmittance.

3. The immunoassay analyzer according to claim 1, wherein
the optical signal is an absorbance,
the discrimination unit compares an absorbance at the main wavelength with an absorbance at the sub-wavelength by determining a ratio (R) between the absorbance (A) at the main wavelength and the absorbance (B) at the sub-wavelength, defined by the following equation (1):

$$R=A/B \qquad (1),$$

the standard value for the magnitude relationship being a standard value (Rs) for the ratio, when the ratio (R) is equal to or larger than the standard value (Rs), the discrimination unit determines that the sample is to be positive, and when the ratio (R) is smaller than the standard value (Rs), the discrimination unit determines that the sample is to be invalid.

4. The immunoassay analyzer according to claim 1, wherein the optical signal is an absorbance, the discrimination unit compares an absorbance at the main wavelength with an absorbance at the sub-wavelength by determining a difference (D) between the absorbance (A) at the main wavelength and the absorbance (B) at the sub-wavelength, defined by the following equation (2):

$$D=A-B \qquad (2),$$

the standard value for the magnitude relationship being a standard value (Ds) for the difference, when the difference (D) is equal to or larger than the standard value (Ds), the discrimination unit determines that sample is to be positive, and when the difference (D) is smaller than the standard value (Ds), the discrimination unit determines that the sample is to be invalid.

5. The immunoassay analyzer according to claim 1, wherein the determination unit determines that the sample is negative when no color change of the sample analysis tool is detected based on a previously determined standard, and the discrimination unit determines whether the detected color change is due to the specific immunoreaction or a cause other than the specific immunoreaction.

6. The immunoassay analyzer according to claim 5, wherein the optical signal is an absorbance, when the absorbance at the main wavelength is smaller than the previously determined standard value, the sample is determined to be negative regarding that no color change in the sample analysis tool is detected, and when the absorbance at the main wavelength is equal to or larger than the standard value, the discrimination unit determines whether the detected color change is due to the specific immunoreaction or a cause other than the specific immunoreaction.

7. The immunoassay analyzer according to claim 1, wherein a wavelength difference between the main wavelength and the sub-wavelength is at least 10 nm.

8. The immunoassay analyzer according to claim 1, wherein the discrimination unit further determines whether the color change due to a cause other than the specific immunoreaction is due to a nonspecific reaction or a cause other than immunoreactions.

9. The immunoassay analyzer according to claim 1, wherein an immobilized antibody or immobilized antigen that can bind to the substance to be detected is immobilized on the measurement region, the sample and a labeled antibody or labeled antigen that can bind to the substance to be detected and is labeled with a label identifiable through color change are present in the measurement region of the sample analysis tool, when the target substance is present in the sample, the labeled antibody or labeled antigen is bound to the immobilized antibody or immobilized antigen via the target substance to form a complex, whereby color change is caused in the measurement region by the label, and the color change in the measurement region is detected by the optical detection unit.

10. The immunoassay analyzer according to claim 9, wherein the label is a colored insoluble carrier particle, and the color change is coloring of the measurement region caused by the formation of the complex containing the colored insoluble carrier particle.

11. The immunoassay analyzer according to claim 9, wherein the label is an enzyme, and the color change is coloring of the measurement region resulting from coloring of a substrate through an enzyme reaction of the substrate and the enzyme contained in the complex.

12. The immunoassay analyzer according to claim 9, wherein there are a plurality of kinds of target substances, a plurality of kinds of immobilized antibodies or immobilized antigens corresponding to the respective target substances are immobilized in the measurement region, and the plurality of kinds of labeled antibodies or labeled antigens corresponding to the respective target substances are present in the measurement region.

13. The immunoassay analyzer according to claim 1, wherein the optical signal measurement unit comprises at least one unit selected from the group consisting of an absorbance measurement unit, a reflectance measurement unit, and a transmittance measurement unit, each for measuring the respective optical signals at the main wavelength and the sub-wavelength.

14. The immunoassay analyzer according to claim 1, wherein the light source portion is selected from the group consisting of a light emitting diode (LED) and a semiconductor laser diode (LD).

15. The immunoassay analyzer according to claim 1, wherein the optical signal measurement unit measures the optical signals irradiated in the measurement region by the light source portion at the main wavelength and the sub-wavelength at a time difference.

16. The immunoassay analyzer according to claim 15, wherein the time difference is no greater than 0.1 seconds.

* * * * *